(12) United States Patent
Mäkipää et al.

(10) Patent No.: US 11,555,620 B2
(45) Date of Patent: Jan. 17, 2023

(54) ELECTRICAL FILTER STRUCTURE

(71) Applicant: Oy Lifa Air Ltd., Helsinki (FI)

(72) Inventors: Janette Mäkipää, Helsinki (FI); Vesa Mäkipää, Helsinki (FI)

(73) Assignee: Oy Lifa Air Ltd, Helsinki (FI)

( * ) Notice: Subject to any disclaimer, the term of this patent is extended or adjusted under 35 U.S.C. 154(b) by 291 days.

(21) Appl. No.: 16/623,797

(22) PCT Filed: Jun. 18, 2018

(86) PCT No.: PCT/FI2018/050474
§ 371 (c)(1),
(2) Date: Dec. 18, 2019

(87) PCT Pub. No.: WO2018/234633
PCT Pub. Date: Dec. 27, 2018

(65) Prior Publication Data
US 2020/0109869 A1    Apr. 9, 2020

(30) Foreign Application Priority Data

Jun. 19, 2017 (FI) ..................................... 20175573

(51) Int. Cl.
*F24D 3/16* (2006.01)
*F24F 8/10* (2021.01)
(Continued)

(52) U.S. Cl.
CPC ............ *F24F 8/10* (2021.01); *B01D 46/0032* (2013.01); *B01D 46/0036* (2013.01); *B01D 46/023* (2013.01); *B01D 46/50* (2013.01); *B01D 53/007* (2013.01); *B01D 53/0407* (2013.01); *B01D 53/8687* (2013.01); *B03C 3/017* (2013.01); *B03C 3/019* (2013.01); *B03C 3/08* (2013.01);
(Continued)

(58) Field of Classification Search
CPC combination set(s) only.
See application file for complete search history.

(56) References Cited

U.S. PATENT DOCUMENTS 1,142,990 A    6/1915   Stern
5,108,470 A    4/1992   Pick
(Continued)

FOREIGN PATENT DOCUMENTS

CN    1812841 A    8/2006
CN    2870990 Y    2/2007
(Continued)

OTHER PUBLICATIONS

Cherrie et al: Effectiveness of face masks used to protect Beijing residents against particulate air pollution. Occup Environ Med, 2018, vol. 75, pp. 446-452.
(Continued)

*Primary Examiner* — Christopher P Jones
*Assistant Examiner* — Sonji Turner
(74) *Attorney, Agent, or Firm* — Laine IP Oy

(57) ABSTRACT

This publication discloses a filter unit connectable to a mobile communication device including a fan for generating an air flow inside the filter unit, electrodes covered with a photo catalytic material like TiO$_2$ in the air flow, UV-LEDs illuminating the electrodes, and outlet for the air flow directed in direction of user of filter unit.

28 Claims, 19 Drawing Sheets

(51) Int. Cl.
*B01D 46/00* (2022.01)
*B01D 46/02* (2006.01)
*B01D 46/50* (2006.01)
*B01D 53/00* (2006.01)
*B01D 53/04* (2006.01)
*B01D 53/86* (2006.01)
*B03C 3/017* (2006.01)
*B03C 3/019* (2006.01)
*B03C 3/08* (2006.01)
*B03C 3/12* (2006.01)
*B03C 3/155* (2006.01)
*B03C 3/36* (2006.01)
*B03C 3/41* (2006.01)
*B03C 3/47* (2006.01)
*B03C 3/86* (2006.01)
*F24F 8/192* (2021.01)
*F24F 8/22* (2021.01)
*F24F 8/167* (2021.01)

(52) U.S. Cl.
CPC ............... *B03C 3/12* (2013.01); *B03C 3/155* (2013.01); *B03C 3/368* (2013.01); *B03C 3/41* (2013.01); *B03C 3/47* (2013.01); *B03C 3/86* (2013.01); *F24F 8/192* (2021.01); *B01D 2253/102* (2013.01); *B01D 2255/20707* (2013.01); *B01D 2255/802* (2013.01); *B01D 2257/91* (2013.01); *B01D 2259/804* (2013.01); *B01D 2279/50* (2013.01); *B03C 2201/04* (2013.01); *F24F 8/167* (2021.01); *F24F 8/22* (2021.01)

(56) References Cited

U.S. PATENT DOCUMENTS

| | | | |
|---|---|---|---|
| 5,403,383 A | 4/1995 | Jaisinghani | |
| 5,549,735 A | 8/1996 | Coppom | |
| 5,593,476 A | 1/1997 | Coppom | |
| 5,993,738 A * | 11/1999 | Goswani | B03C 3/60 422/4 |
| 6,042,637 A * | 3/2000 | Weinberg | B03C 3/38 96/97 |
| 6,387,844 B1 | 5/2002 | Fujishima et al. | |
| 6,589,489 B2 * | 7/2003 | Morrow | C01B 13/10 422/186.04 |
| 6,632,407 B1 * | 10/2003 | Lau | C01B 13/115 422/186 |
| 6,939,611 B2 | 9/2005 | Fujishima et al. | |
| 7,160,363 B2 * | 1/2007 | Kulmala | B03C 3/155 96/84 |
| 7,309,664 B1 * | 12/2007 | Marzolin | C03C 25/42 428/905 |
| 7,740,810 B2 * | 6/2010 | Hay | B01D 53/007 422/186.04 |
| 8,263,012 B2 * | 9/2012 | Hay | B60H 3/0608 422/186.04 |
| 9,737,895 B2 | 8/2017 | Genereux et al. | |
| 2005/0175518 A1 * | 8/2005 | Lin | B01D 53/885 422/186.3 |
| 2005/0223899 A1 | 10/2005 | Kulmala et al. | |
| 2005/0238551 A1 | 10/2005 | Snyder et al. | |
| 2007/0253860 A1 * | 11/2007 | Schroder | A61L 9/22 422/4 |
| 2008/0170971 A1 | 7/2008 | Bergeron et al. | |
| 2009/0010801 A1 * | 1/2009 | Murphy | B03C 3/016 422/4 |
| 2011/0072770 A1 | 3/2011 | Lakdawala et al. | |
| 2012/0093691 A1 | 4/2012 | Mole | |
| 2012/0207647 A1 | 8/2012 | Kim | |
| 2013/0074690 A1 | 3/2013 | Tomimatsu et al. | |
| 2015/0224218 A1 | 8/2015 | Burnett | |
| 2015/0290478 A1 | 10/2015 | Curran | |
| 2017/0080373 A1 | 3/2017 | Engelhard | |
| 2017/0106218 A1 | 4/2017 | Lin et al. | |
| 2017/0120182 A1 | 5/2017 | Kim | |

FOREIGN PATENT DOCUMENTS

| | | |
|---|---|---|
| CN | 202569888 U | 12/2012 |
| CN | 203140156 U | 8/2013 |
| CN | 104197410 A | 12/2014 |
| CN | 106552469 A | 4/2017 |
| CN | 106622662 A | 5/2017 |
| CN | 106765658 A | 5/2017 |
| CN | 206884671 U | 1/2018 |
| EP | 1492622 B1 | 7/2014 |
| JP | 2016002545 A | 1/2016 |
| KR | 20150142971 A | 12/2015 |
| WO | WO9822222 A1 | 5/1998 |
| WO | WO0220162 A2 | 3/2002 |
| WO | WO02073094 A1 | 9/2002 |
| WO | WO03084665 A1 | 10/2003 |
| WO | WO2005014053 A2 | 2/2005 |
| WO | WO2007070704 A2 | 6/2007 |

OTHER PUBLICATIONS

Yao: Principle, design and application of air purification. China Science and Technology Press, Sep. 30, 2014.

\* cited by examiner

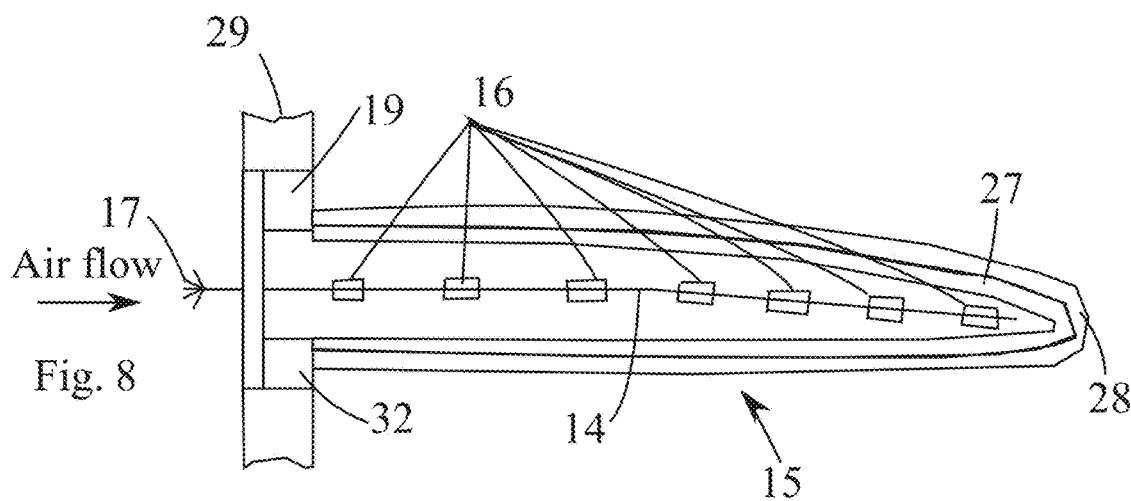
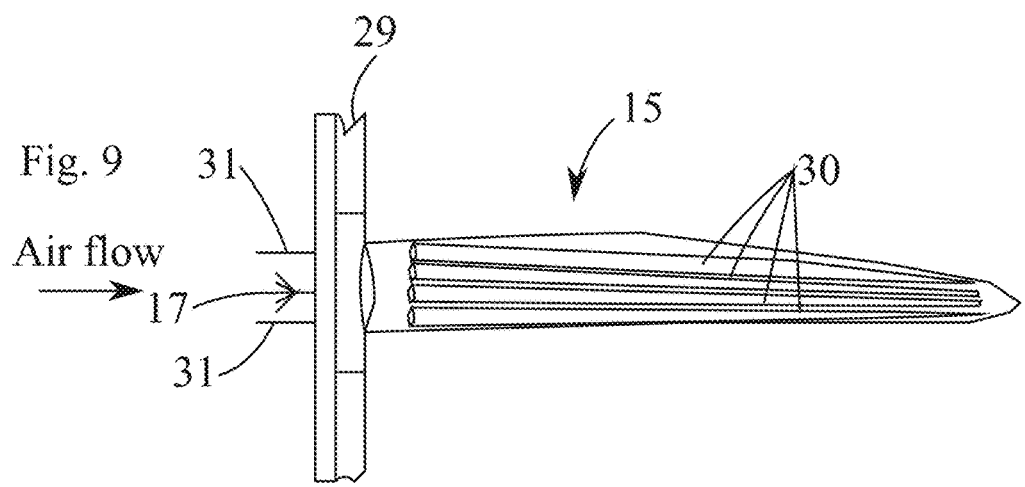
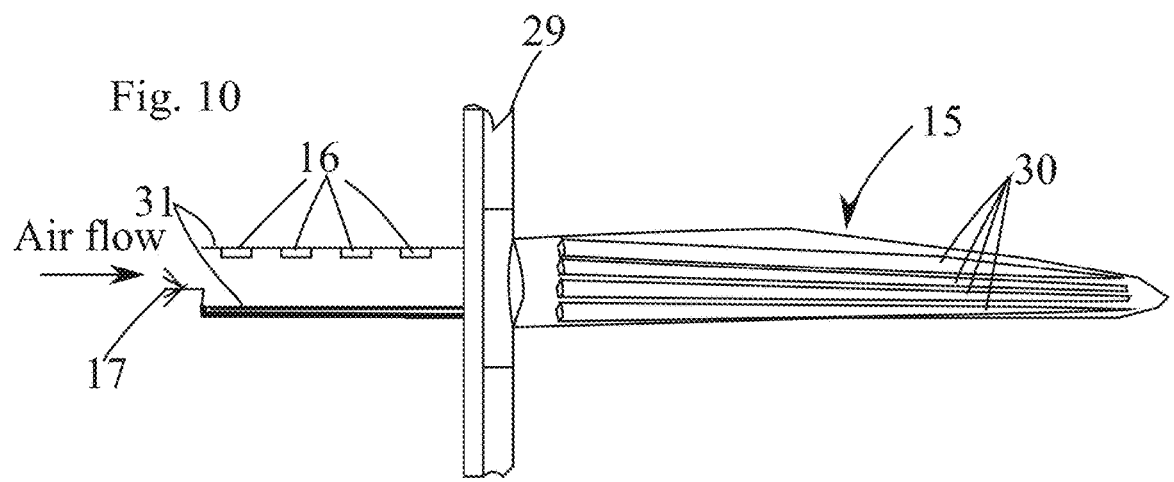

Air flow

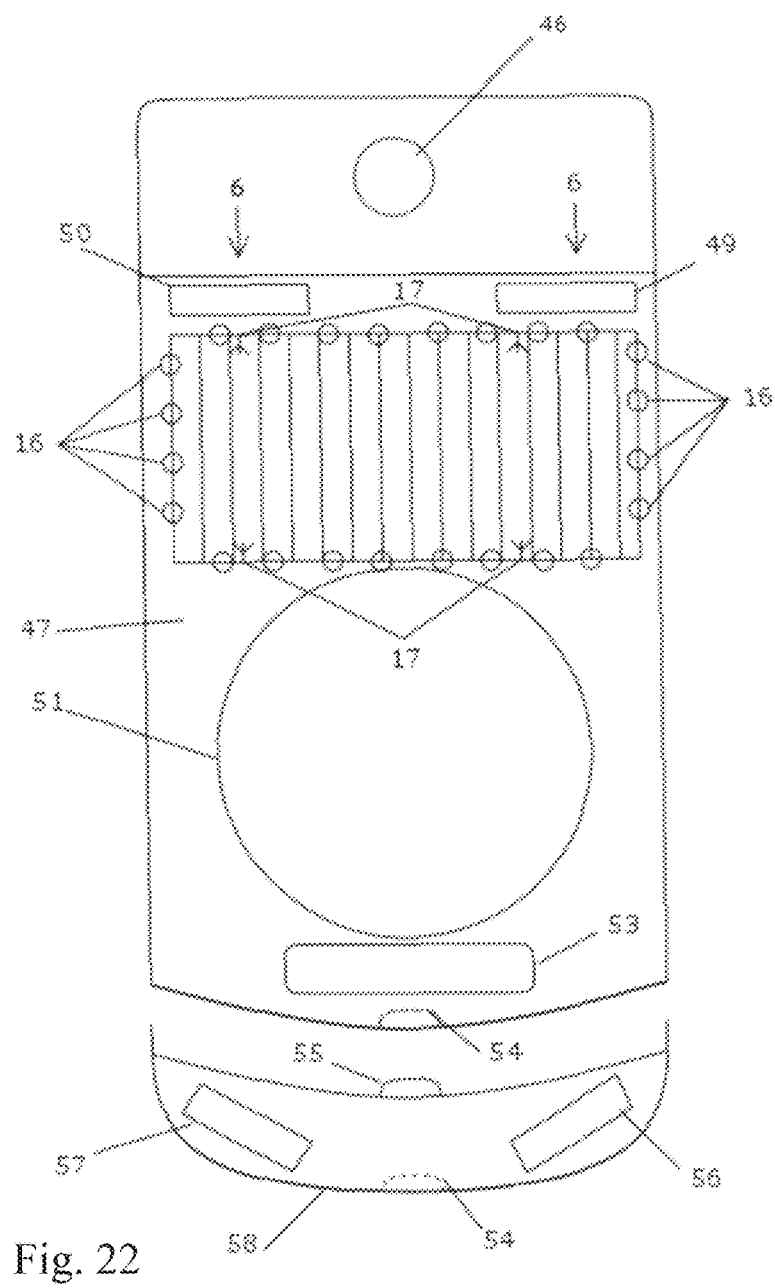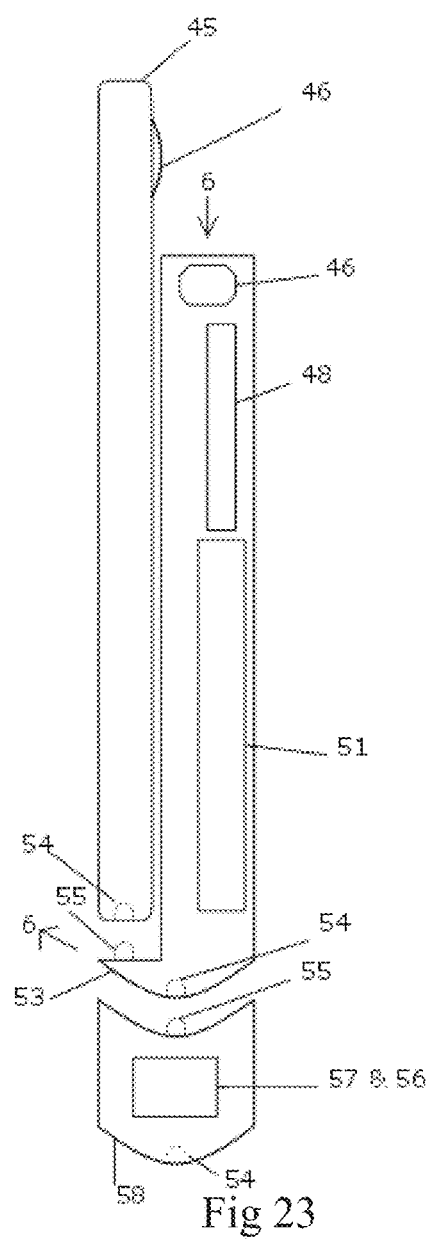
Fig. 22
Fig 23

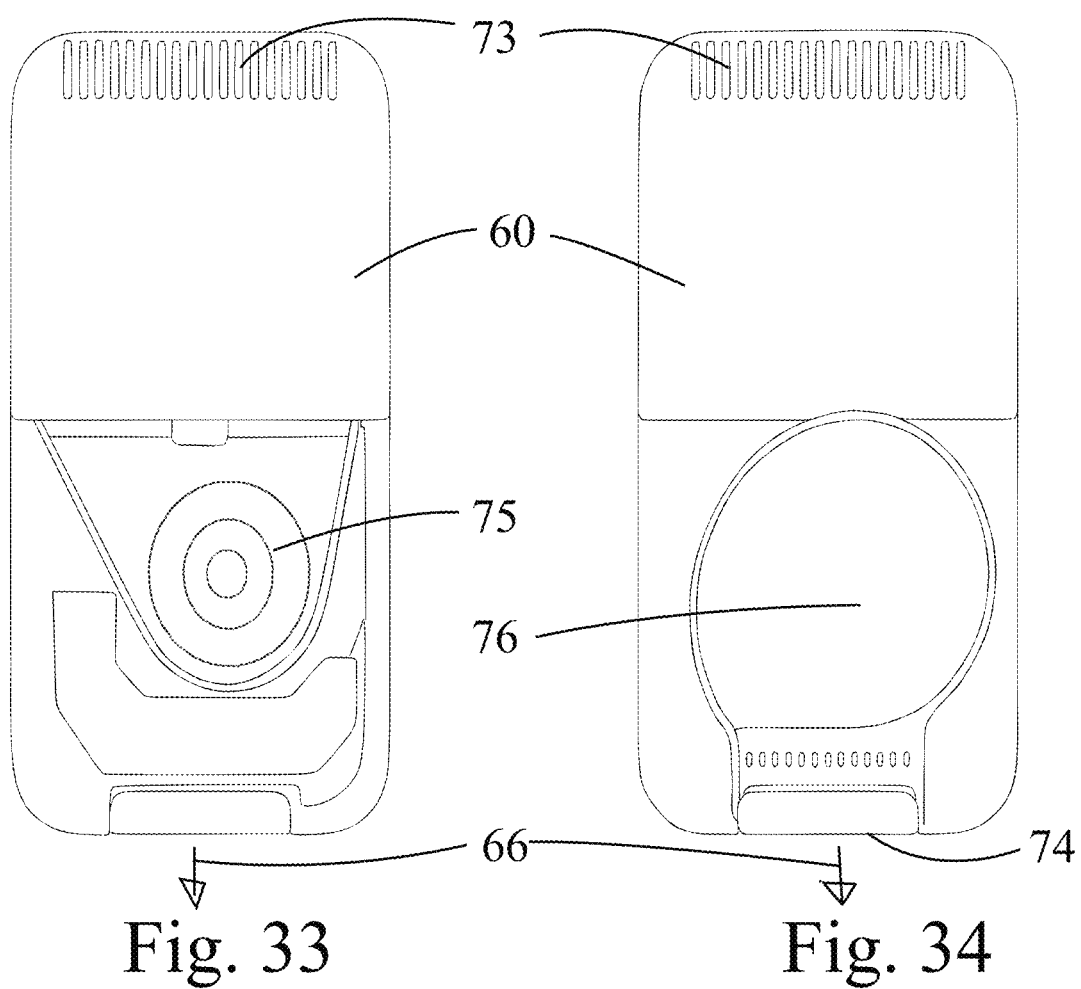
Fig. 33    Fig. 34
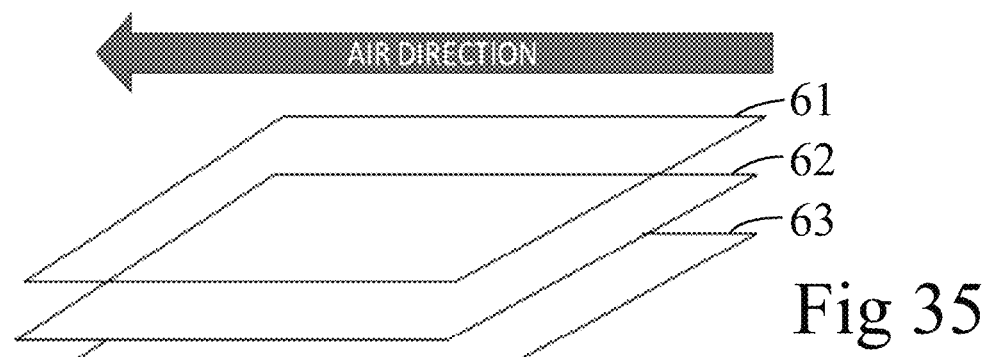
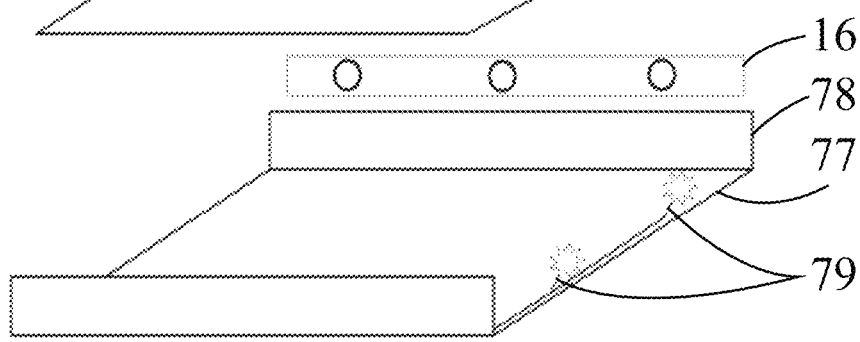
Fig 35

ELECTRICAL FILTER STRUCTURE

The present invention relates to an electrostatic filter construction including gas and particle filters according to the preamble of claim 1.

Consciousness of air impurities and the health hazards caused by them has increased considerably in recent years. Research has shown that gaseous and particulate impurities are environmental exposure agents that clearly increase sickness and health hazards. The problems are worst in large cities, in which emissions from traffic and energy production pollute the air. Besides their health hazards, impurities in outdoor air also affect the corrosion and oxidation of materials.

Attempts are made to reduce the impurities travelling from outside to the indoor air of buildings and vehicles by filtering the incoming air. Nowadays, the replacement air for dwellings, offices, and commercial buildings is cleaned mainly using only particle filters; gases are filtered mainly only in special cases (e.g., clean rooms, electrical and electronics rooms).

The separation ability of particle filters varies greatly depending of the size of the particles. Fibre filters separate particles well if they are more than 5 µm, such as, for example, pollens. However, most of the emissions from traffic and energy production are small particles (particle size less than 1 µm), which are much more difficult to filter.

One effective way to filter small particles is the electrostatic precipitator shown in FIG. 1, the operation of which is based on an electrically charged particle and the force exerted by an electrical field on the particle. In conventional two-stage electrostatic precipitators used in air-conditioning applications, the airflow and the particles in it are first led through a charger section 1, in which they are charged electrically. The figure shows the corona wires 4 and the path 3 of the ions. After this, the airflow travels to a collector section 2, which is formed of alternating collector 9 and high-voltage electrodes 81, according to FIG. 1. The figure shows the path of a positively charged particle 5 from the filter. The corona voltage value is typically +8 kV and the collector plate value +4 kV. The distance between the plates is typically in the order of 5 mm, so that a normally sized cell contains about 100 plates. Drawbacks with an electrostatic precipitator are the complexity of the solution and its subsequent expensiveness. At the same time, the dust collecting on the collector plates can cause spark-overs, which lead to the production of unhealthy ozone, an unpleasant sound, and a temporary weakening of the filtering efficiency.

According to FIG. 2, electrostatic precipitation can also be applied to a fibre filter. The particles are charge in the same way as in the electrostatic precipitator, but the collection section 2 is formed of a fibre filter 7, above which a power electrical field is arranged with the aid of a metal mesh 7. This solution too does not eliminate the ozone production problem. The metal mesh 7 has no filtering properties.

Recently, combination filters have appeared on the market, which filter gases and particles. However, the small-particle separation efficiency of combination filters is quite modest. They generally belong to the fine filter class (F5-F9) 10 µm>Dp>1 µm in EN779 standard, which means, for example, that they filter a half or less of the 0,3-µm particles). The ability of the filters to charge gases is very modest in relation to the nominal airflow. U.S. Pat. No. 5,108,470 (Charging element having odour and gas absorbing properties for an electrostatic air filter) discloses a filter, in which a flat electrode containing activated carbon is located between two filter structures. The activated-carbon electrode is connected to an electrical power circuit. The construction is surrounded by metal electrodes, which have no filtering properties. The filter construction is at right angles to the direction of flow.

Application WO 98/22222 (Device in connection with an electrostatic filter) in turn discloses placing a fibre filter between two or more activated-carbon electrodes. In this case, the direction of the flow is parallel to the electrodes.

A general problem with flat-plate filter solutions is the small amount of gas filtering material: for the filter to be able to effectively separate gaseous impurities, the transit time through the filter material should be sufficiently long. The small amount of adsorptive material means that the charging capacity of the solutions described for gaseous impurities remains low. For this reason, the filters have a short service life. By adding consecutive filtering stages, the gas filtering ability of the alternatives referred to above can be increased, but at the same time the pressure drop will increase.

The capacity of a gas filter can be increased by using a corrugated construction, as disclosed in U.S. Pat. No. 5,549, 735 (Electrostatic fibrous filter). The patent discloses a solution, in which there is a charger section, a high-voltage electrode with the same polarity as the charger section, and an earthed activated carbon electrode. The high voltage is used to form an electrical field between the metal mesh and the activated carbon electrode.

The metal mesh does not have filtering properties. It is difficult to make an even electrical field, because close to the tops of the corrugations the distance of the electrodes easily differs from what it is in the flat section. When making the creases, the upper and lower parts of the corrugations must be sealed. In addition, the parts must be impermeable to air, because the upper and lower parts do not participate in filtering.

To produce clean incoming air, a filter must be able to filter not only small particles, but also gaseous impurities. One problem is the pressure drop over the filter: present solutions cannot provide effective particle and gas filtering simultaneously with a low pressure drop. Effective filtering is also expensive to implement. In practice, this means that existing air-conditioning machinery would require more powerful and also noisier fans, in order to compensate for the pressure drop caused by the additional filtering. An increasing pressure drop over the filter will require a corresponding increase in fan energy, thus correspondingly increasing the power consumption of the fans.

WO0220162 and U.S. Pat. No. 5,403,383 describe other prior art electrical filters.

EP 03712196 describes an electrostatic filter structure with bag like filters for filtering both gases and particles.

The present invention is the first mobile phone integrated clean air skin protection and clean air breathing device. It utilizes advanced PECO photoelectric oxidation and PCO Photocatalytic oxidation with mechanical filtration as electrostatic filter construction including gas and particle filters.

It is an ideal solution to be used in areas where clean and purified air is not otherwise available and risks for polluted air and/or inhaling of pathogens is elevated like in outdoors, crowded areas, places with inefficient ventilation, restrooms, elevator cabins, public transportation hubs and vehicles, industrial environments, construction sites, educational-, hospitality- and healthcare facilities.

It is also related with improvement of beautiful face skin and improved social capacities.

Researches have shown that gaseous and particulate impurities are environmental exposure agents that clearly increase sickness and health hazards. The problems are worst in large cities, in which emissions from traffic and energy production pollute the air. Besides their health hazards, impurities in indoors and outdoors air also affect the corrosion and oxidation of materials. Industrial facilities and this transportation network generate pollutants such as carbon dioxide, nitrogen oxides, sulfur dioxide, and particulate matter. This air pollution increases oxidative stress in the human body. Oxidative stress occurs when there is an imbalance in our cells due to either an increase in free radicals and/or a decrease in antioxidants. Pollution from industrial and transportation sources may increase the amount of free radicals in the body. Over time this disruption in the balance between free radicals and antioxidants can injure our tissues. Oxidative stress has been linked to a number of illnesses, including some forms of cancer, cardiovascular disease, obesity, diabetes, Alzheimer's disease, eye diseases, and lupus.

The increase in air pollution over the years has had major effects on the human skin. Various air pollutants such as ultraviolet radiation, polycyclic aromatic hydrocarbons, volatile organic compounds, oxides, particulate matter, ozone and cigarette smoke affects the skin as it is the outermost barrier. Air pollutants damage the skin by inducing oxidative stress. Although human skin acts as a biological shield against pro-oxidative chemicals and physical air pollutants, prolonged or repetitive exposure to high levels of these pollutants may have profound negative effects on the skin. Exposure to ultraviolet radiation has been associated with extrinsic skin aging and skin cancers. Cigarette smoke contributes to premature aging and an increase in the incidence of psoriasis, acne and skin cancers. It is also implicated in allergic skin conditions such as atopic dermatitis and eczema. Polyaromatic hydrocarbons are associated with extrinsic skin aging, pigmentation, cancers and acneiform eruptions. Volatile organic compounds have been associated with atopic dermatitis. Given the increasing levels of air pollution and its detrimental effects on the skin, it is advisable to use strategies to decrease air pollution Source; 'Effects of air pollution on the skin: A review Poonam Puri, Shashi Kumar Nandar, Sushruta Kathuria, V. Ramesh'

This invention is designed to reduce face skin aging by preventing and/or reducing polluted air to be contacted with face. In a case that polluted air will pass through clean air barrier this invention can be used to rinse pollutant off from skin and hair and by using same temperature for air intake and filtered, exhausted air there is no drying effect to face skin. Air distribution to breathing zone is widened to cover whole face and velocity is adjusted to lower face skin temperature enabling lower temperature to face, sweat glands will stay open. Otherwise if the sweat cannot get out, it may build up under the skin, causing rash and tiny, itchy bumps and when the bumps burst and release sweat, many people feel a prickly sensation on their skin.

Air-purifying respirators are used against particulates, gases, and vapours. Negative-pressure respirators using mechanical filters with or without chemical media are normally used for protection against environmental pollutants and spreading of diseases like in U.S. Pat. No. 1,142,990 (A) Positive-pressure units such as powered air-purifying respirators (PAPRs) are mainly used for occupational health purposes for breathing protection to enable easy breathing with high filtration efficiency. (US2015290478 (A1)

Filtering face masks available to consumers may be ineffective against air pollution. Although a mask may filter tiny particles as advertised, face size and shape as well as movement can lead to leakage as high as 68 percent, researchers report in Occupational & Environmental Medicine.

Source:
Cherrie J W, Apsley A, Cowie H, et al. Effectiveness of face masks used to protect Beijing residents against particulate air pollution. Occupational and Environmental Medicine 2018; 75:446-452.

In addition to the airways, the eyes can also be affected by air pollution. The ocular surface is directly in contact with the environment and is therefore the most exposed to air pollutants.

Some infections are spread when an infected person talks, breathes, coughs or sneezes tiny particles containing infectious agents into the air. These are called small particle aerosols. Due to their tiny size, small particle aerosols can travel long distances on air currents and remain suspended in the air for minutes to hours. These small particle aerosols may be breathed in by another person. Germs can enter the body through the respiratory tract and eyes. Examples of airborne spread diseases: The common cold, Influenza, Chickenpox, Mumps, Measles, Whooping cough (pertussis), Tuberculosis (TB) and Diphtheria.

Face masks provide limited protection against airborne diseases and pollutants due to reasons named above such as leakages, no protection to eyes etc.

Use of filtering face masks reduces facial recognition. It's expected (IHS market) that number of surveillance cameras only in China will reach 626 million units in 2020, thus there are several reasons to identify people with surveillance cameras use of filtering face mask in public places is facing potential ban or use will be restricted to be allowed only for acceptable health related reasons.

There are also available to have personal air purifiers that are using negative ions claiming that solution can create personal breathing zone by pulling pollutants away from discharge. In U.S. Pat. No. 9,737,895 B2, Personal rechargeable portable ionic air purifier, in summary is mention that it will controllably provide ions to energise and to clean personal airspace. In real life there are always some air movement and just by ionizing air from one point it is impossible to secure clean air breathing zone. In the case if ionizer really works as promised the clothes of user, his skin, air passages and hairs should be loaded with viruses, bacteria's, moulds etc. that with negative ions weighted particles will drop down, also to personal breathing zone. Negative ionic air purifiers can't filter particle or gaseous contaminants if collection section for ionized airflow is missing. In this patent is also shown in FIGS. 7A and 7B how invention can be used inside mask—then particle pollutants that has passed masks will be, based on negative ions, easier get stuck to respiratory system.

Attempts are made to reduce the impurities travelling from outside to the indoor air of buildings and vehicles by filtering the incoming air. Air flows in indoors are difficult to control. Indoors should have slightly positive pressure inside to prevent outdoor pollutants penetrate inside but this happens very rarely thus buildings are leaking and in mechanical exhaust ventilation (like in residential buildings kitchen hoods and restrooms vents) is actually dragging polluted air from outdoor creating negative pressure inside. This negative pressure can be turn to neutral or positive pressure with supply air but in practice in most of the buildings sufficient supply air is either missing or fresh air from outdoor is not filtered properly. In Finland supply air flow in living area is 0.5 l/s per square meter and minimum extract air for kitchen is 20 l/s for bathroom 15 l/s and for toilet 10 l/s.

Invention is easy to use and carry with thus it's convenient to be used with mobile phones, carried in neck strap portable or installed on a table or any other surface and used as a stand alone air purifier. One application is to install it inside baby pram, stroller and infant car seats and create positive pressure inside cover with clean air. Same attachment method allows invention to be used either permanently or only temporary for several usages and with almost all surfaces.

This invention reduces spreading of airborne diseases and protects respiratory systems and eyes to be infected by air pollutants by creating personal clean air breathing zone. It also enables full facial recognition when using it in public places. The invention is to create an entirely new type of filtration combining advantageously mechanical gas and particle filter and PCO filtration (UVA radiation and surface Nano coating with catalyst like TiO2 and when ionising the air end result is PECO (photo electrochemical oxidation). In patent WO2005014053A2 PHOTOELECTROCHEMICAL AIR DISINFECTION solution as described in patent is suitable to be used mainly in general HVAC system and air ducts.

With the invention at least part of the drawbacks of the prior art referred to above can be eliminated.

The invention is based on the fact that with wave like filters the electrodes which are positioned substantially parallel to the direction of flow of the gas are equipped with ultraviolet light sources and covered with photo catalytic material like TiO2. In some advantageous solutions brush like elements are used in the charging unit.

This invention is also based on fact that photo catalytic reaction will materialize only when air is in contact with photo catalytic material that has needed energy dosage of the ultraviolet light radiation. In this invention air is forced to contact $TiO_2$ or other catalyst grounded or covered electrodes by using opposite polarity than high voltage unit ionizing the air before it.

Considerable advantages are gained with the aid of the invention.

With the aid of this invention, air (or some other gas) is cleaned effectively of both 10 gaseous and particulate impurities and with photo catalytic reaction the contaminations of the air can be decomposed and the filters can be sterilized. With the wave like filters and longitudinal electrodes and light sources the photo catalytic effect can be prolonged to the maximum.

When using thick and stretchy electret filter media folding of the filter media is not available without affecting electret, therefore in this invention filter media can be assembled with automatic production line by using poles in bottom and top part of filter casing and inset tightly. This enables mass scale manufacturing with low costs and without using any glue or other fixative.

Filter casing bottom and sides are from electrically conductive material. Filter materials are coated with $TiO_2$, Ag or similar Nano catalyst. Filter casing is from UVA penetrable plastic sheet having uniform distribution of UVA led light. Similar sheet is above filter casing and between plastic sheets there is paper to separate UV-LED light illumination to both sides which can be reflective in order to further enhance photocatalytic reaction. Casing sheets can be also coated with Nano catalyst. Negative ions can be discharged from carbon fibres inside or in front of filter casing in order to accelerate photocatalytic reaction.

When air purifiers (e.g. mobile communication devices in this invention) are equipped with $CO_2$ sensors, carbon dioxide levels can adjust the speed of fan automatically. These units are designated to be close enough users face for enabling clean breathing zone. The $CO_2$ sensor can detect elevated CO2 level and fan will operate faster. When $CO_2$ level is low, air purifier goes to standby mode in order to save energy.

Invention in mobile communication units can be used by billions of users and it will create personal clean breathing zone, wherever they are.

Air purifiers are adapted to the markets as globally with various penetration rates. Gas filters in air purifiers are usually done from activated carbon and/or impregnated activated carbon. Often microbiological growth in activated carbon is causing odour problem and gas filter media is emitting odours instead of adsorbing them. Microbe VOCs can be harmful and for sensitive groups even fatal. This also causes loss of money when handling customers claim, hurts companies brand and jeopardize credibility of the whole indoor air quality industry. With this invention microbiological growth in filter media will be prevented.

Air purifiers are adapted to the markets as globally with various penetration rates. Gas filters in air purifiers are usually done from activated carbon and/or impregnated activated carbon. Often microbiological growth in activated carbon is causing odour problem and gas filter media is emitting odours instead of adsorbing them. Microbe VOCs can be harmful and for sensitive groups even fatal. This also causes loss of money when handling customers claim, hurts companies brand and jeopardize credibility of the whole indoor air quality industry. With this invention microbiological growth in filter media will be prevented.

FIG. 3 shows a solution according to EP 03712196. In the filter, electrical forces are exploited by charging the particles with the aid of a corona discharge produced, for example, using corona wires 4, and collected with the aid of an electrical field in a collector unit 2. In the charger unit 10 and the collector unit 2, voltages of the order of 8-10 kV can be used. With the aid of the electrical forces, effective filtering can be achieved for small particles too, without high pressure drops.

In this solution both electrodes 14 and 82 are manufactured from activated carbon, or some other material containing a substance that filters gases, and which has a low electrical conductivity. In this case, a material with a low electrical conductivity refers to a material with a surface resistance in the order of $10^9$-$10^{15}$ Ohms.

In order to bring the electrical filtering effect to a sufficient level, there should be a high difference in voltage potential between the electrodes 14 and 82. This can be implemented in two ways, but in practice a simple construction is one in which the electrode 14 is connected to a high voltage and the electrode 82 is earthed according to FIG. 3. This electrode can also be left floating, though this may weaken the filtering effect.

Also photo catalytic filter structures are known. However in these solutions because of free air flow with high air speed, energy dosage will be not enough to enable to destroy DNA structure of living organism inside ventilation systems. Alternatively if such arrangement will be installed inside air handling unit both initial investment and running costs are very high.

Most of the UV-lights used for HVAC industry are Mercury Lamp types (Hg, Hg—Fe, and Hg—Ga) having high radiation efficiency with high energy consumption. In addition, mercury lamps are very bad for the environment.

Based on done measurements bag filter with 300 mm deep pocket have following UVC-light density:

1,000 $\mu W/cm^2$=1,000 $mW/cm^2$ or 10 W/m2

9 cm from UV-light inside filter bag pocket, density was 650 µW/cm$^2$ 18 cm from UV-light inside filter bag pocket, density was 400 µW/cm$^2$ Filters used inside Air Handling Units are normally 600 mm deep, often having several bends, thus density will be in several areas, at least in the bottom part of the pocket 0 µW/cm$^2$.

Similarly when using UVA- and/or UVB-lights and TiO2 or similar catalyst on inner filter surface inside of bag filter pockets, energy dosage needed for photocatalytic reaction cannot be reached caused by poor achievability of radiation.

The invention is to create an entirely new type of gas and particle filter, advantageously to be used in connection with a mobile communication device. With the invention at least part of the drawbacks of the prior art referred to above can be eliminated.

The invention is based on the fact that with bag like filters the electrodes which are positioned substantially parallel to the direction of flow of the gas are equipped with ultraviolet light sources and covered with photo catalytic material like TiO$_2$. In some advantageous solutions brush like elements are used in the charging unit.

This invention is also based on fact that photo catalytic reaction will materialize only when air is in contact with photo catalytic material, that has needed energy dosage of the ultraviolet light radiation. In this invention air is forced to contact TiO$_2$ or other catalyst covered electrodes by using opposite polarity than high voltage unit ionizing the air before it.

More specifically, the particle filter according to the invention is characterized by what is stated in the characterizing portion of claim 1.

Considerable advantages are gained with the aid of the invention.

With the aid of this invention, air (or some other gas) is cleaned effectively of both gaseous and particulate impurities and with photo catalytic reaction the contaminations of the air can be decomposed and the filter bags can be sterilized. With the bag like filters and longitudinal electrodes and light sources the photo catalytic effect can be prolonged to the maximum. The construction also permits a solution with a low pressure drop. For this reason, the filter can be installed in existing ventilation systems, without changes being required in the fans. Filter bags can also be installed in every direction without the risks of bending bags. In addition to having low operating costs, the solution is also economical to implement.

When connected to existing fans in HVAC system or air purifiers, (e.g. mobile communication devices as in this invention) the filtration system can be used automatically with sensors that monitor and adjust the functions. Fans are equipped with automatic speed control that accelerates the fan according to increased power consumption, which is caused by increased pressure drop due to dust loading of filter. The calculation of increased energy consumption can be utilized to determine when the filter should be changed. This calculation can be also used to increase output current in high voltage unit(s) for ionizing and in electrodes to ensure sufficient filtration efficiency through the whole lifespan of the consumable filters.

When air purifiers (e.g. mobile communication devices in this invention) are equipped with CO$_2$ sensors, carbon dioxide levels can adjust the speed of fan automatically. These units are designated to be close enough users face for enabling clean breathing zone. The CO$_2$ sensor can detect elevated CO$_2$ level and fan will operate faster. When CO$_2$ level is low, air purifier goes to standby mode in order to save energy.

The benefits of the solutions are:
effective combined gas and particle filtering,
a long service life, if used as a filter for individual rooms,
a low pressure drop and thus low energy costs,
control of the production of the deleterious ozone that appears in electrostatic filters: the gas filter removes the ozone that arises in the corona discharge,
elimination of the need for filter-cell cleaning that arises in electrostatic filters: dirtied filters are changed frequently,
manufacture of the construction is simple and economical,
the used replaceable component can be manufactured from materials that can be disposed of by e.g. burning,
the fibre filter also acts as the insulating material for the electrodes.
electrodes can be filters
invention in mobile communication units can be used by billions of users and it will create personal clean breathing zone, wherever they are.

This invention can be used in Air Handling Units (AHU), in supply and exhaust air ventilation, in fresh air ventilation and in air purifiers.

When invention is used for cleaning the air in exhausted air in kitchen hoods and/or exhaust ducts, it can keep kitchen exhaust ventilation system clean. Invention will increase fire safety, enhance occupational safety, save energy and increase employee and customer satisfaction within commercial kitchens but it can be used in domestic purposes too. The use of invention will significantly diminish the need for kitchen exhaust cleaning, which will improve occupational safety, make the cleaning process more comfortable, cheaper and safer. As the ducts will remain cleaner, fire safety is also improved, which creates a better and safer work environment.

There are several parties that are benefiting results of the new innovation. All citizens in urban area will get rid of smells caused by kitchens and they will get healthy benefit thus spreading of unhealthy ozone can be avoided. Property owners will diminish risks of fire and get lower cost of fire insurance for their facilities and also cleaning costs of exhaust ducts will drop dramatically. Kitchen user, usually restaurant operator, will get benefit from very short cleaning time thus operation time of kitchen can be maximized.

In many countries there are no existing, obligatory laws for cleaning kitchen exhaust systems. In naturally ventilated houses accumulation of grease and oil in exhaust duct will create pressure loss and designed exhaust air volumes cannot be reached—this leads high level of particles inside homes, causing serious health problems even deaths. Complains in residential buildings are often related with smells of cooking or tobacco smoke. Kitchen exhausting system is the main channel to vent out air from homes—and unfortunately there are normally lot of leakages in exhaust air ducts. By installing invention and replacing it within reasonable frequency, spreading of particles and smells can be avoided.

Commercial kitchen exhaust systems consist of a kitchen hood, exhaust ducts and an exhaust fan. Kitchen hoods are equipped with grease filters that are designed to capture the heat, smoke, odours, grease and grease vapours produced in the cooking process (RPPA). The filters need to be frequently cleaned and even if they are maintained well by the restaurant personnel, there will always be grease and dust that flow through the filter into the exhaust ducts. This is because the grease particles can be very small (<5 microns) and the air velocity as well as the temperature at the hood area are very high. This grease and dust accumulates inside the exhaust ducts as it cools down, forming a major fire hazard. To reduce the fire risk the grease and dust accumulations must be removed from the duct. This is not a simple task. Grease duct cleaning must be done by experts, it is time consuming, occupationally unsafe, expensive and environmentally very unsustainable. It requires the use of products such as of toxic substances, very alkali washing detergents, brushes, different bristles, water, disposable cloths, demanding personal protective equipment and so on. These are problems invention is here to solve. Instead of relying on unsafe, expensive, unsustainable methods, it will provide a product to prevent grease from ever reaching the exhaust ducts. Not only is the invention safer and cheaper than current applications, it is also an economically more sustainable application.

Invention as a grease collecting solution is to be installed into the kitchen hood and/or exhaust duct. Invention will increase fire safety, enhance occupational safety and improve the marketing value for commercial kitchens. The use of invention will remove or at least significantly diminish the need of kitchen exhaust duct cleaning while improving the fire safety in the kitchen. The invention will save energy and remove small particles, reducing odour complains and thus improve property value and client and employee satisfaction.

Currently both clients and contractors are dissatisfied of current commercial kitchen exhaust duct cleaning methods. Contractors who provide cleaning services have reported of unwillingness to engage in grease duct cleaning services as it was regarded grimy and potentially unsafe. Clients complained that cleaning companies tend to create harm to the clients' working conditions by, for example, spreading grease from exhaust ducts to the kitchen areas. As a solution, electrostatic precipitators are installed in kitchen exhaust. However, most of these are taken out of use, as this solution proved to not be practical. It was noted the units need to be cleaned too often, which is too costly and time consuming and thus distract regular kitchen operations. There are also other existing practices such as ozone treatment with UV-lights and cyclone type grease filters. With all these existing solutions end result is that exhaust ventilation system is, even after taken on use solution mention above, having accumulated amount of grease and oil thus those need to be cleaned within variable periods. As a conclusion, before this invention a cost-effective solution to prevent accumulation of oil and grease in kitchens is non-existing.

Commercial kitchens benefit from invention in many ways. It increases the wellbeing of the staff, since it improves the ventilation hygiene, by decreasing the odours. By decreasing odors client satisfaction will also rise, as more customers find the restaurant environment enjoyable, since there are no unpleasant odours. This again brings value to the kitchen, now that more customers will be coming in. Thirdly, as the odour complaints diminish, the neighbourhood value will rise, which brings up property value, benefitting the landlord.

In addition the staff don't need to be concerned of the kitchen exhaust system catching fire. It extends the kitchen hood filters cleaning frequency, which frees up time from the staff and they can spend their time and energy on doing what they do best: preparing and providing delicious meals. In addition to energy savings already mentioned, one embodiment of the invention enables exhaust ventilation system to be clean and operate efficiently leading to lower energy consumption.

The owner of the premise, usually the restaurant owner, is responsible for maintaining the kitchen exhaust system. Kitchen hood filters are usually maintained and kept clean by the restaurant personnel, but the duct and exhaust fan cleaning needs to be done by trained professionals. The current methods of cleaning make it an unwanted job full of occupational safety hazards, environmentally unfriendly substances, massive amounts of disposables as well as waste of energy, time and money. Ducts need to be inspected and cleaned at least once a year depending on the country's/state's legislation and the usage. In USA they need to be cleaned between 1 to 12 times a year which causes several thousands in expenses for the restaurant. Toxic washing detergents are used to remove the grease, which makes it impossible to utilize the grease in for example biofuel production. With the invention the restaurants will have significantly less expenses, since the need of duct cleaning decreases due to the solution utilized in the product, which prevents the grease from getting further to the ducts, thus the customers will receive a cost efficient solution to improve their fire safety and sustainability.

In the following, the invention is examined with the aid of examples and with reference to the accompanying drawings.

FIG. 8 shows as a cross sectional view one filter element in accordance with the invention.

FIG. 9 shows as a cross sectional view another filter element.

FIG. 10 shows as a cross sectional view another filter element in accordance with the invention.

FIG. 22 shows a back view of an embodiment of the invention where the filter unit is combined with a mobile phone.

FIG. 23 shows a side view of the embodiment of FIG. 22.

FIGS. 33-34 show the air flow of filter units described in FIGS. 28-32.

FIGS. 35-38 show the structure of the removable particle filter casing in more detail.

Figure 1:
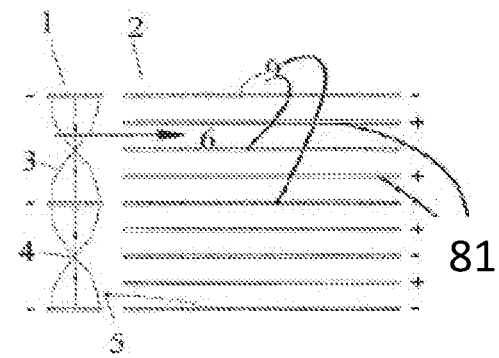
FIG. 1 shows a schematic diagram of one filter solution according to the prior art.
Figure 2:
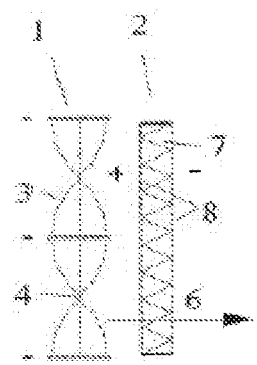
FIG. 2 shows a schematic diagram of a second filter according to the prior art.
Figure 3:
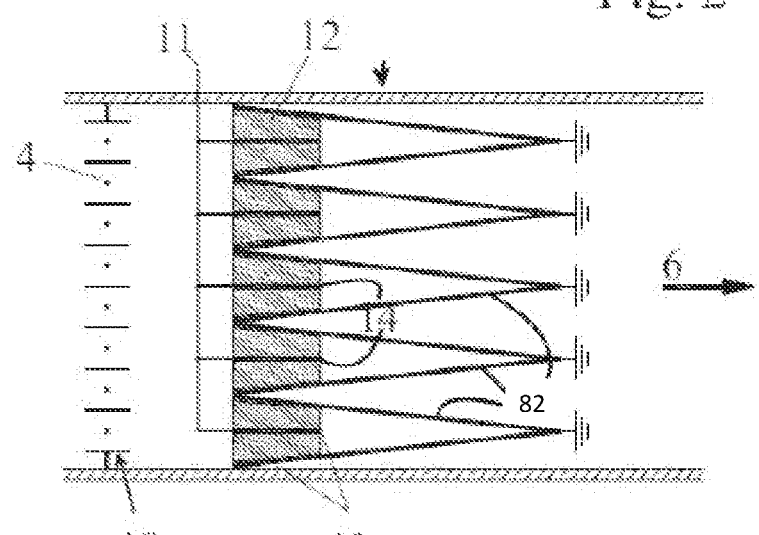
FIG. 3 shows a schematic diagram of the filter solution according to the prior art.
Figure 4:
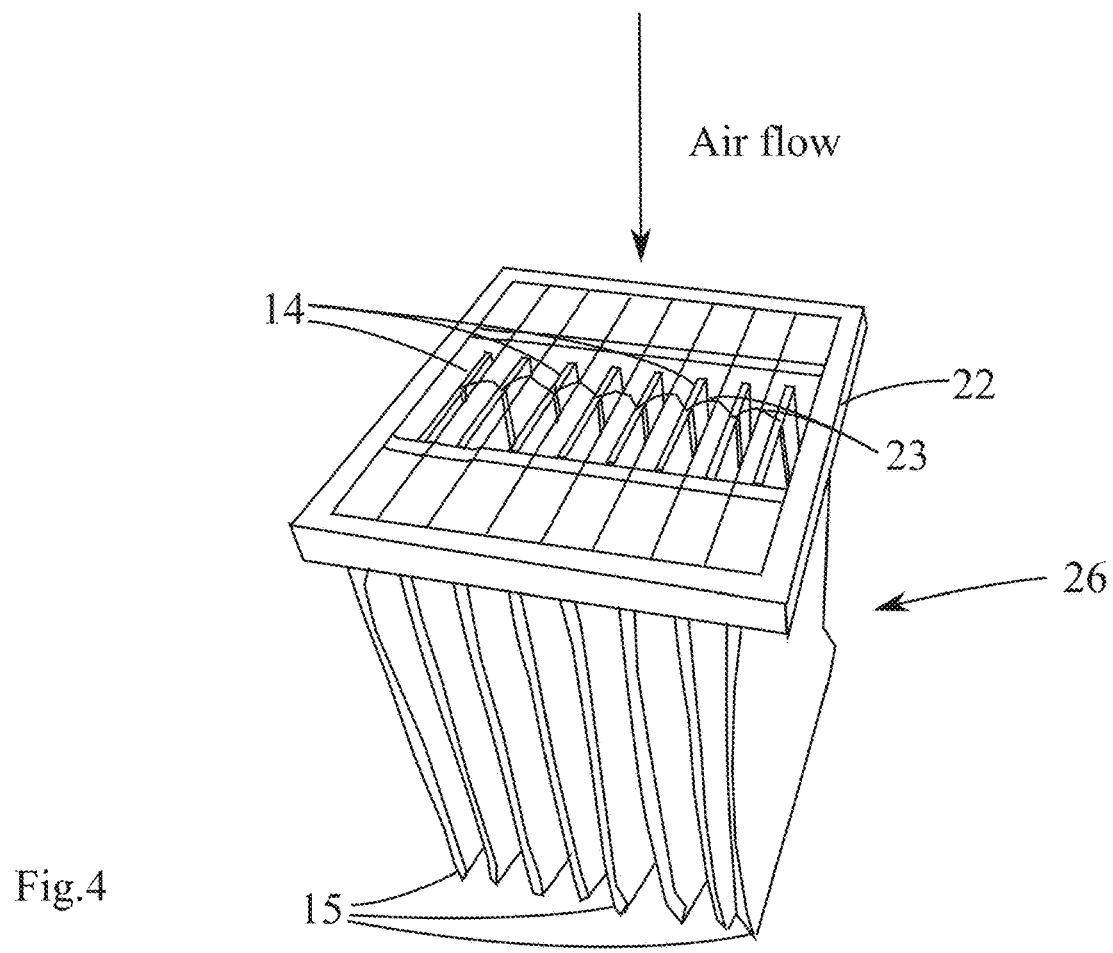
FIG. 4 shows a filter solution according to the invention.

In the following, the invention is examined with the aid of the following terms:
1 charging section
2 separation section, electrostatic filter
3 ion path
4 corona wire
5 positively charged particle
6 air flow
7 fibre filter
8 metal mesh
9 separation plate
10 charging unit
11 high voltage
12 fibre filter
13 activated carbon filter
14 positive metal electrode of the activated carbon filter or $TiO_2$ covered electrodes
15 filter bag/filter element
16 UV-light sources
17 corona brushes
18 Cover plate of the charging unit
19 High voltage unit
20 Corona strip
21 Corona strip insulators
22 Frame of the electrode unit
23 Wirings of the electrodes 14 and UV-light sources
24 Support poles for the electrodes 14
25 Electrode unit
26 Filter bag unit
27 Particle filter media
28 Gas filter media
29 Filter mounting frame
30 Sub-filters
31 Grounding
32 UV-transformer
33 Positive voltage transformer
34 Positive voltage electrodes
35 Input for positive voltage
36 Protective grid in AHU solution
37 High voltage sockets
38 Corrugated filter media
39 Contactor for grounding
40 Contact for high voltage
41 Contact for high voltage
42 Fixed mounting rail
43 Adjustable mounting rail
44 Charging unit frame
45 Mobile communication device, mobile phone
46 Camera optics
47 portable filter unit
48 Removable particle filter casing
49 Transformer
50 High voltage unit
51 Fan
52 Support bar
53 Outlet for the air flow
54 Plug in
55 Plug
56 Particle sensor
57 $CO_2$ sensor
58 Monitor unit
60 Filter cover (UV-a can pass)
61 Plastic sheet with dot matrix printing for spreading UV-illumination evenly to whole sheet
62 thin paper between plastic sheets
63 lid of filter material, transparent
64 folded filter material
65 main printed circuit board (PCB)
67 USB-A-port for using the unit 47 as a charger
68 micro-USB-port for charging the battery 72
69 LED-indicator (on/off/filter change)
71 Magnets for attaching to the mobile device
72 Battery
73 intake grill
74 slider for adjusting the direction of the output air flow
75 intake chamber of the fan
76 output chamber of the fan
77 filter casing bottom
78 filter casing sides
79 carbon fibers for negative ion input
80 guiding pins for filter material 64
81 electrode
82 electrode In accordance with one preferred embodiment of the invention in FIG. 4 is presented a combined filter 26 and electrode unit 25 mounted together. In operation the structure is surrounded from all sides by a ventilation duct and air flows from top to bottom in accordance with the arrow in the figure.

Electrodes 14 are positioned parallel to the air flow and covered with a suitable photo catalytic material like $TiO_2$. The electrodes 14 are typically aluminium, also other metals or other electrically conductive material may be used. On these electrode plates are positioned UV-light sources 16 on both sides of the electrode. These light sources 16 are typically LED (Light emitting Diodes) light sources assembled on suitable substrate, in this case a longitudinal circuit board extending deep into the filter bag 15. Typically the light source elements are as long as the electrodes 14. On the other hand the electrodes 14 extend almost to the end of the filter bags 15. The ratio of the length of the electrode 14 to the length of the filter bag 15 is typically around 70%, advantageously in the range of 50-95%. Wiring 23 feeds energy to the light sources 16 and as well takes care of the grounding of the electrodes 14.

Using UV-C light LED lights are installed on both sides of electrode. The main target with UV-C radiation is to destroy DNA structure of the organic material captured to the filter media. UV-A and UV-B light can also be installed in both sides of electrodes and be mainly used for photo-catalytic oxidation.

Using UV-A and UV-B led lights can also be installed inside between electrode plates (FIGS. 24-25) that must be then transparent enabling uv-light to penetrate through plates. These plates can have either honeycomb, mesh wire or nanostructure like graphene or other nano layer type structure to enhance surface area for $TiO_2$ or other catalyst above flat plates. Only electrode plate's inner side against UV-light will not be coated with $TiO_2$, all other surfaces (Electrode plates outer side and structures integrated in it) will be coated with anatase phase or combination of anatase and rutile phase of $TiO_2$. Other catalyst can also be used. Amount of LED-light depends on the usage of the filter solution, distance to catalyst and PCO efficiency needed The efficiency of LED light is measured in lumens per watt, which refers to the total quantity of light the LED lamp produces per 1 W of energy. Efficiency=total lumen output/total power.

These light sources 16 are typically LED (Light emitting Diodes) light sources assembled on suitable substrate, in this case a longitudinal circuit board extending deep into the filter bag 15. Typically the light source elements are slightly shorter than electrodes 14. On the other hand the electrodes 14 extend almost to the end of the filter bags 15.

In one preferred embodiment of the invention the filter bag unit 26 (without the charging unit 25) is disposable, in other words the filter bags 15 will not be cleaned but replaced by a new unit when dirty. This saves essentially maintenance time and cost.

Photo catalytic material like $TiO_2$ may also be positioned in the filter bags 15 with suitable process like with wet and dry methods. In the wet method, the nano-$TiO_2$ in anatase phase of $TiO_2$ is in liquid solution which is sprayed onto the substrate. In the dry method the anatase phase of $TiO_2$ is in powder form and then led through the substrate material. Nano-coating methods such as spraying, dipping and ultra sound treating may be used.

Figure 5:
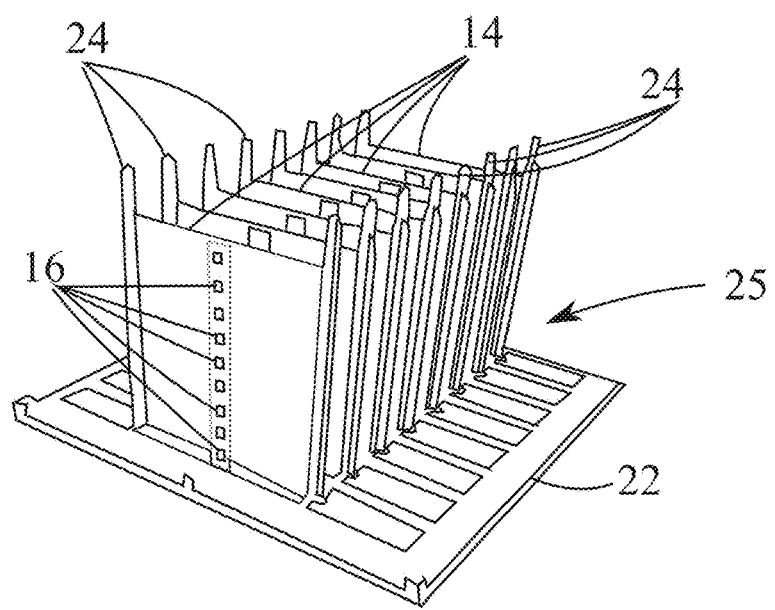
FIG. 5 shows the electrode element of FIG. 4.

First filter media to against UV-light source will be treated with photo catalyst and it can be:
non woven activated carbon filter media
electret filter material
coarse filter material
combination and or mix of the filter material named above
other filter material In FIG. 5 can be seen an electrode unit 25 turned upside down such that and UV light sources 16 are visible. The electrodes 14 are positioned between support poles 24, which keep the elastic filter bags 15 in suitable form. The frame 22 may be e.g. plastic. As can be seen from the figure one preferred embodiment includes 8 electrodes 14 and correspondingly 8 filter bags 15. Of course the number of electrode/bag pairs can vary, typically in range of 4-12.

Figure 6:
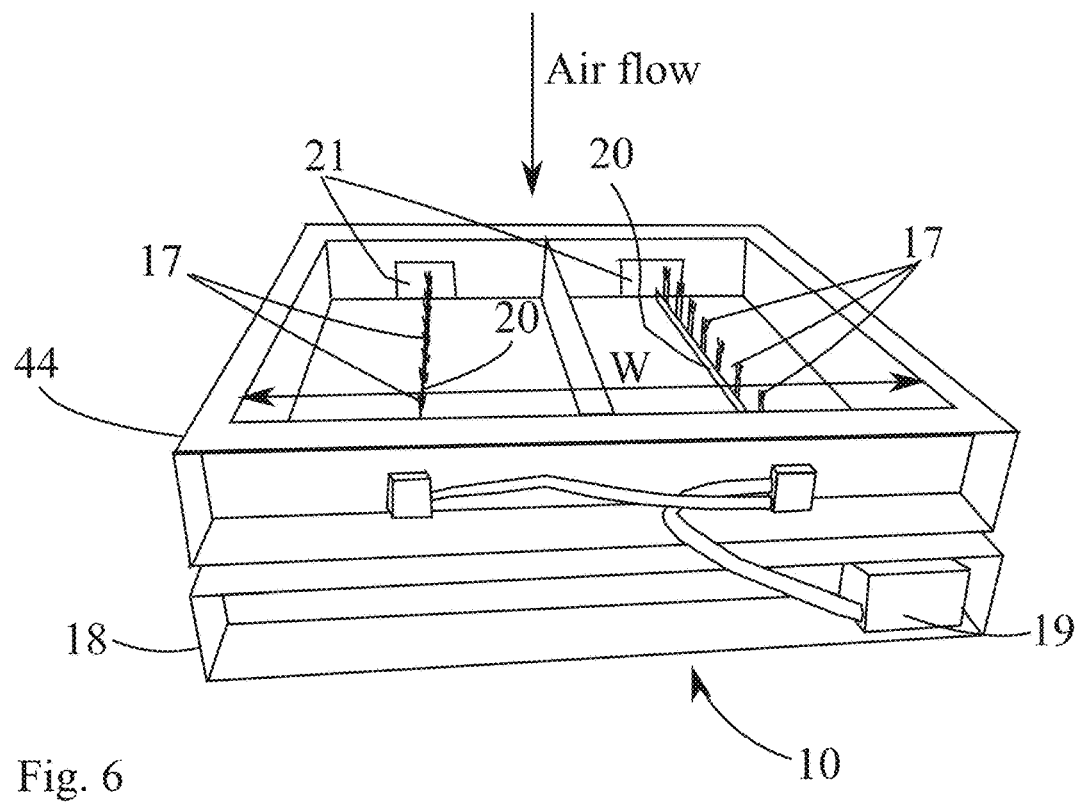
FIG. 6 shows the charging unit according to the invention.

In accordance with FIG. 6 the charging unit 10 comprises a frame 44, which is typically aluminium. Inside of the frame 44 are positioned corona strips 20 equipped with brush like extensions 17 directed against the air flow. These extensions have activated carbon fibre brushes 17 on the top. In this way the first thing high voltage item the air flow meets are these carbon fibre brushes 17. By this feature wear of the corona elements can be minimized. In this solution there are two parallel electrically conductive corona strips 20 positioned such that each strip 20 is located about 25% of the total width W away from the inside of the frame 44, where W is the total width of the inside of the frame 44. The number of corona strips 20 increases if the inner cross section (face) of charging unit 10 increases. On the other hand each brush 17 has a limited area of influence and therefore a charging unit 10 (as well as the filter structure 2) with a larger cross section (face) needs more brushes 17.

The frame 44 is typically square, also rectangle form for the frame 44 is a possible form for the frame 44. High voltage is input to the to the corona strips 20 from high voltage unit 19 of the charging unit 10. The high voltage is typically negatively charged. The corona strips 20 are insulated from the frame 44 by insulators 21. During operation cover unit 18 will be placed into the frame 44.

In operation the charging unit 10 will be placed above the construction of FIG. 4 such that the incoming air will first meet the charging unit 10 and then electrode 25 and filter bag unit 26.

Figure 7:
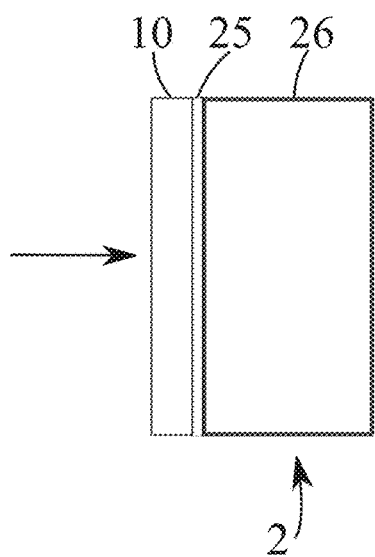
FIG. 7 shows as a block diagram one embodiment of the invention.

FIG. 7 shows an overall concept of the invention. The arrow shows the direction of the air flow. First in the air flow is the charging unit 10, next charging unit 10 and finally bag unit 26 with filter bags.

The above described filter construction is a new effective solution to purify particle and gaseous contaminants. This invention can be used as integrated air purifier when installed in ventilation system for purifying fresh-, re-circulated or exhaust air. It can also be installed inside a casing with fan and power supply as a stand-alone air purifier.

Invention can be used to replace regular filters used in Air Handling Units (AHU) having following functions: It will charge the air airflow thus enhance capturing efficiency for particles, it has photo catalytic oxidation function (PCO) as well as sterilizing ones too.

Inside filter bag's frame is installed for charging the airflow, high voltage unit (input 220-240 V, 50/60 Hz, output 12V or 24V with 6-15 kV) and for LED UV-light, electronic transformer (input 220-240 V, 50/60 Hz, output 12V).

Filter bag 15 has supporting poles 24 inside pockets where electrodes 14 (material can be varied) are positioned and are coated with a photo catalytic material like $TiO_2$ that is photo catalytically active with UV-light (here can be used, based on purpose A, B or C-UV light or combination of lights. LED UV-lights 16 are connected to the electrodes 14 such that they are close to (0.5-20 mm) to the filter media.

The filter bags 15 and electrodes 14 can be electrically connected together with connectors, thus only one electric cable connection and earth cable connection is needed to one filter bag 15/electrode 14. When installing filterbags inside AHU, existing filter frame can be used without any change—only 220/240 V and earth cable need to be connected.

In advantageous embodiments of the invention the invention includes filter bags 15, charger unit 10 and a photo catalytic element with UV-light sources 16 and photo catalytic material, e.g. $TiO_2$. Further, the filter bags 15 are advantageously disposable.

In accordance with FIG. 8 in one preferred embodiment of the invention each bag filter element 15 of the bag unit 26 of FIG. 4 comprises of an aluminium electrode 14 extending to the bottom or almost to the bottom of the bag filter element 15. The electrode 14 is covered with photo catalytic material like $TiO_2$ and also has UV-light sources 16 on both sides of the electrode. Advantageously the electrode 14 is grounded to earth potential. The incoming air is charged by high negative voltage by brushes 17 fed by high voltage unit 19 and the UV-lights 16 are fed by transformer 32 with low voltage. The bag filters 15 typically comprise at least two layers namely particle filter media 27 as inner structure for capturing small impurities in particle for and a gas filter media layer 28 as an outer structure for capturing gaseous materials. The gas filter media layer may be e.g. activated carbon. The media layers 27 and 28 may be combined together e.g. by ultrasonic welding. The bag like filters 15 are mounted in a filter mounting frame 29 side by side as can be seen from FIG. 4 in order to cover the complete inner cross section (face) of the filter structure 2. In this solution the inside of bag 27 may be alternatively covered with $TiO_2$ or the $TiO_2$ cover may be in both the surfaces of the bag 27 and the electrodes 14.

In accordance with FIG. 9 a basic solution is presented where such a filter 15 is used comprising multiple sub-filters 30 inside the main filter bag. Also here the filter 15 is mounted to filter mounting frame in the same way as in FIG. 4. In the incoming air is positioned charging unit with brushes 17 and grounding elements 31 like earthed metal plates. Here the charging unit may be assembled to existing filter structures.

FIG. 10 is a modification of FIG. 9 such that each filter element 15 has a designated photo catalytic element in front of them in the air flow path in form of UV-lights 16 and grounded metal plates 31 with photo catalytic material like $TiO_2$. In addition the structure comprises charging brushes 17 isolated electrically from the grounding elements 31.

Anatase phase TiO2 band gap is 3.2 eV.

Installing LED based UV lamps are much cheaper but light density is low thus they must be installed nearby surfaces to be radiated.

This invention has very small initial investment cost and low running costs comparing the existing separate solution available in the market.

Figure 11:
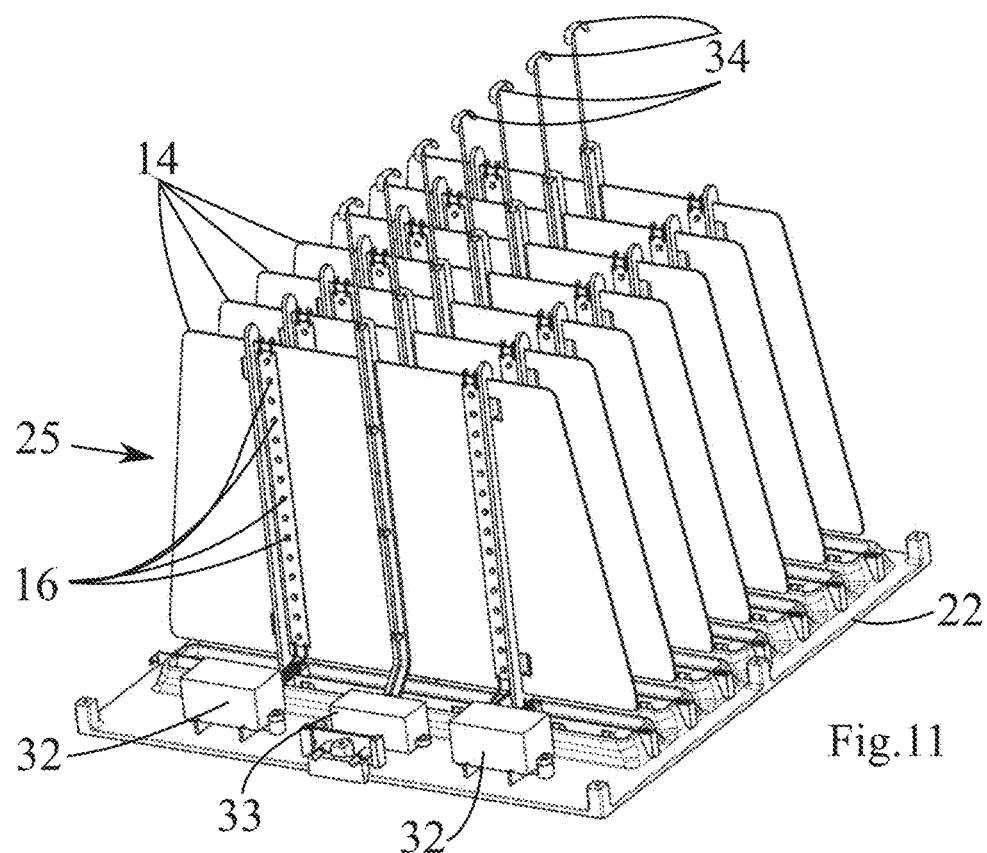
FIG. 11 shows another embodiment of the charging unit of FIG. 5.
Figure 12:
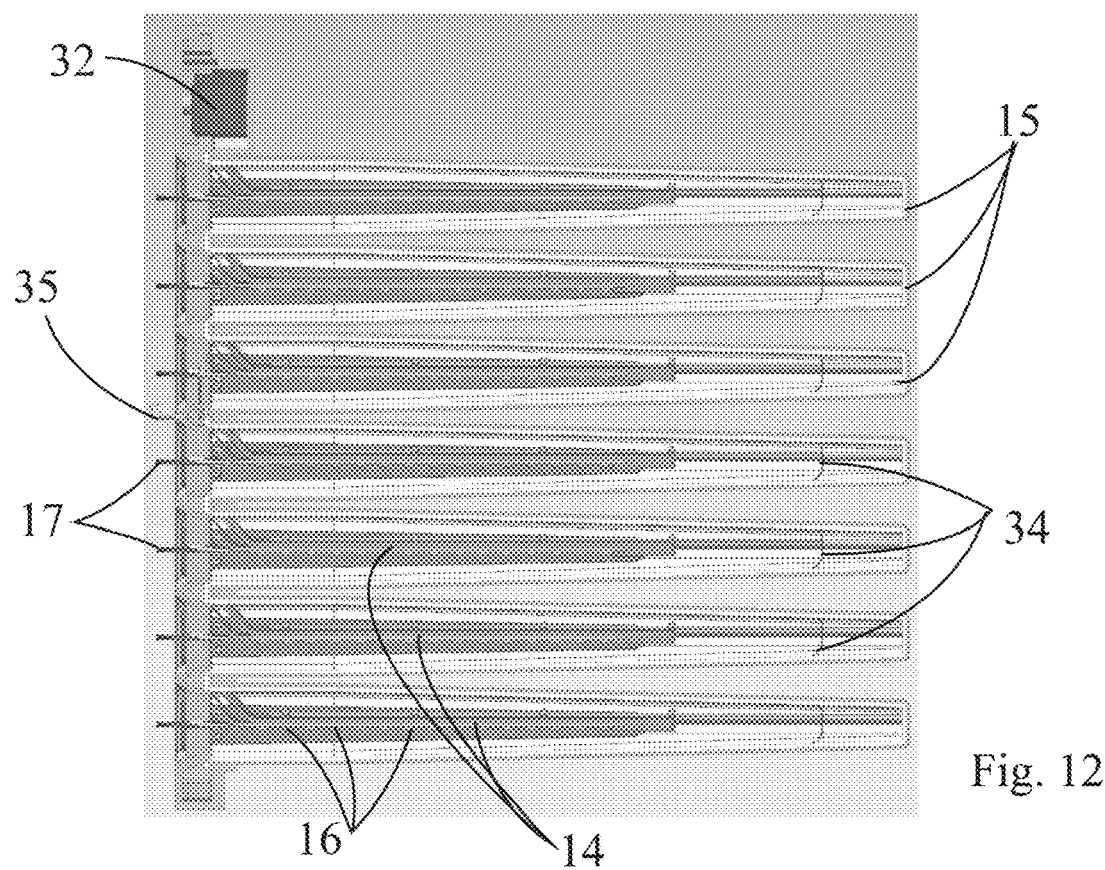
FIG. 12 shows a cross section of the charging unit of FIG. 11 positioned inside the filter bag unit in accordance with the invention.
Figure 13:
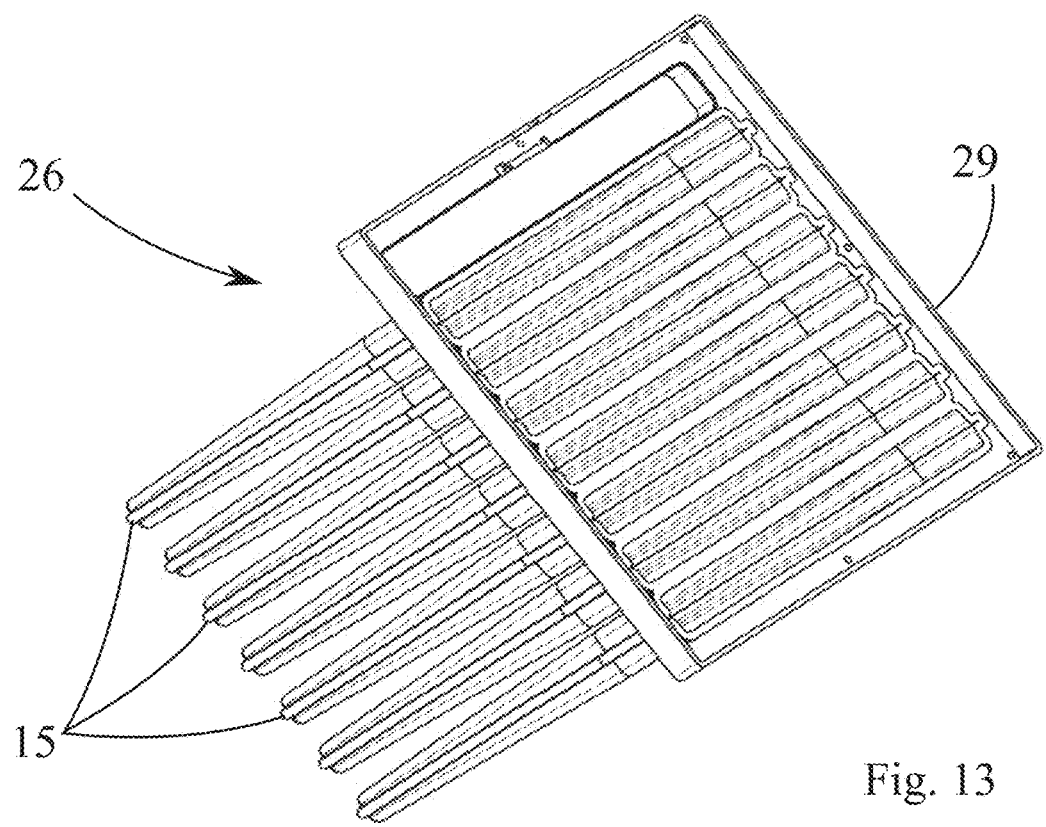
FIG. 13 shows a filter bag unit in accordance with the invention.

In FIGS. 11 and 12 are presented an embodiment where the electrode unit 25 is equipped with a positive electrode structure 34 for each of the electrodes 14 such that the tip of this electrode structure charges the insides of the filter bags 15 of FIG. 12 with positive charge of around 1 kV. The voltage depends on the material of the bag 15 as well as the mechanical properties of the tip of the electrode structure 34. These electrodes 34 are fed with a transformer 33, which gets its input from connector 35 of FIG. 12. The electrodes 14 are typically grounded and isolated from the positive electrodes 34. In FIG. 11 there are two rows of UV-light sources 16 on both sides of the electrodes 14. In accordance with the invention there could be even two additional rows of these UV-light sources 16 on both sides of the electrodes 14 positioned for example on the outer sides of the electrodes 14, in other words in the left and right sides of each electrode in FIG. 11 such that maximum area onside the filter bags 15 would be illuminated by the UV-light. These UV-light sources 16 are fed by UV-transformers 32. Also here the inside of the bag filters 15 may be covered with $TiO_2$.

As can be seen from FIG. 12 the filter bags 15 may have two bags inside each other like in FIG. 8 however the inner bag must be at least partially conductive in order to charge it with positive voltage.

Figure 14:
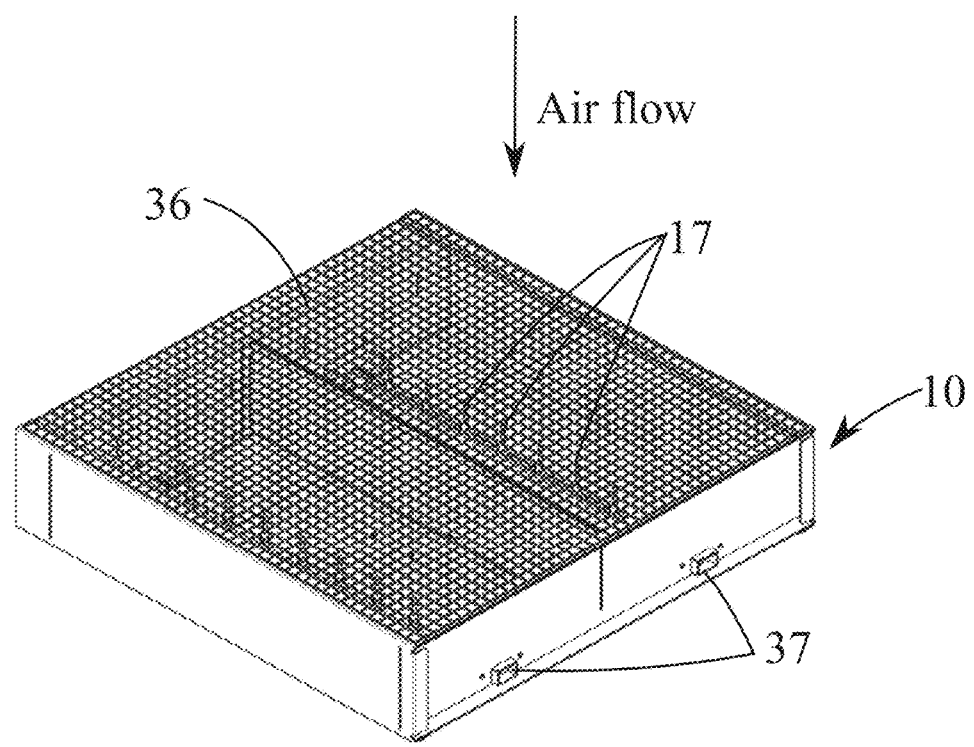
FIG. 14 shows another charging unit in accordance with the invention.

FIGS. 12 and 14 show also the corona brushes 17 for negative charging of the air flow.

The bags materials may be the following:
Inner bag 27 (FIG. 8)
Coarse filter, typically 250-500 g/m²
Outer bag 28 (FIG. 8)
Fine filter, typically 100-250 g/m²
The referred classifications are based on EN799 standard can be found e.g. on the web site of the WHO.:

Particulate matter in ISO 16890 describes a size fraction of the natural aerosol (liquid and solid particles) suspended in ambient air. The symbol ePMx describes the efficiency of an air cleaning device to particles with an optical diameter between 0.3 μm and x μm. The following particle size ranges are used in the ISO 16890 series for the listed efficiency values.

Optical particle diameter size ranges for the definition of the efficiencies, ePMx

| Efficiency | Size range, μm |
|---|---|
| ePM10 | $0.3 \leq x \leq 10$ |
| ePM2.5 | $0.3 \leq x \leq 2.5$ |
| ePM1 | $0.3 \leq x \leq 1$ |

These materials may be impregnated for removal/adsorption/absorption of different gases, one for $SO_2$ and the other for $NO_X$.

The inner media bag 27, which can also be the only filter bag, can be impregnated by $TiO_2$ for better photo catalytic oxidation function. It can also be impregnated against gases PCO is not effective enough. There are several alternatives for suitable combinations of substrates/impregnates. Some are
non woven activated carbon filter media
electret filter material
coarse filter material
combination of above mention filter materials.

Like for sulphur dioxide impregnation can be done by various methods using different impregnates like KOH and $KMnO_4$. The impregnation process can be done with wet and dry methods. In the wet method the impregnant is in water solution which is sprayed onto the substrate. In the dry method the impregnant in powder form is aerosolised and then led through the substrate material.

The capacity of the gas filter is related to the mass of impregnant deposited on the substrate material. On the other hand, the deposited impregnant increases the pressure drop of the fibrous filter, or may reduce the adsorption capacity of other gaseous impurities in case of impregnation of the non-woven activated carbon substrate. Therefore the optimum amount of impregnant depends on the impregnant/substrate combination.

By using filter bags 15 with dimension 592*592*592 mm one filter unit with 10 bags would have 7 m² filter surface. With ten 500*500 mm² electrodes 14 covered on both sides with $TiO^2$ in each filter bag 15 each filter unit would have 5 m² $TiO_2$ covered surface.

FIG. 14 shows a filter bag unit 26 without the charging unit 10. In this embodiment the corona brushes 17 are protected by a protective grid 38 in order to avoid electric shocks of maintenance personnel. The complete housing of the charging unit 10 is advantageously grounded. High voltage is fed to the corona brushes 17 through high voltage sockets 37.

Figure 15:
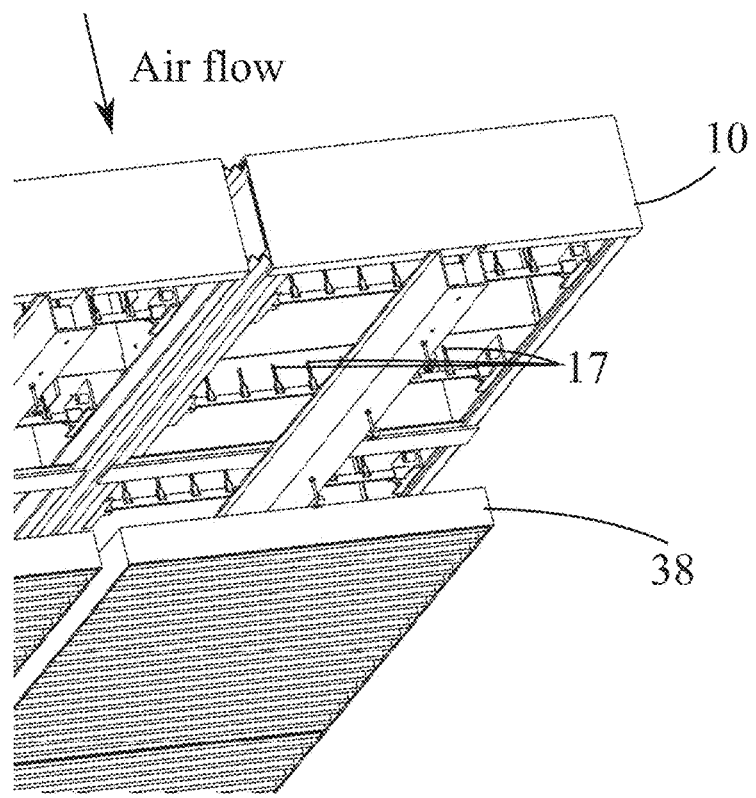
FIG. 15 shows a filter construction where several charging units of FIG. 14 are combined together and combined with a filter construction.
Figure 16:
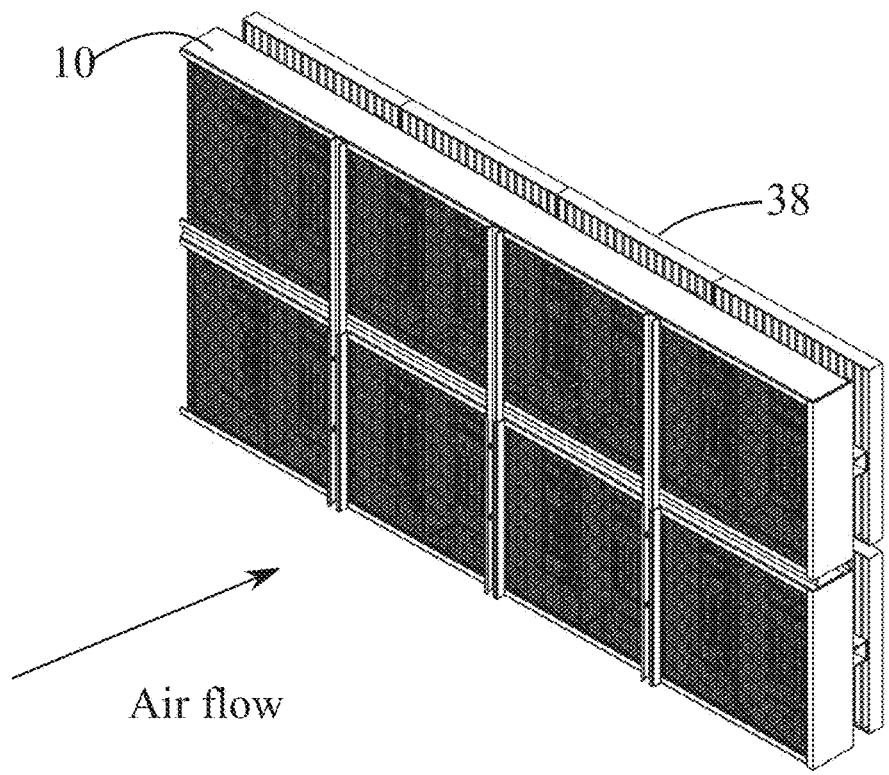
FIG. 16 shows a filter construction of FIG. 15 where the filter unit is assembled to the charging unit.

FIGS. 15 and 16 show a charging and filter unit, where several charging units 10 are combined as a wall to fit different sizes of ventilation ducts. Filter units 38 in form of corrugated filter media are positioned after the charging units including the corona brushes 17.

Figure 17:
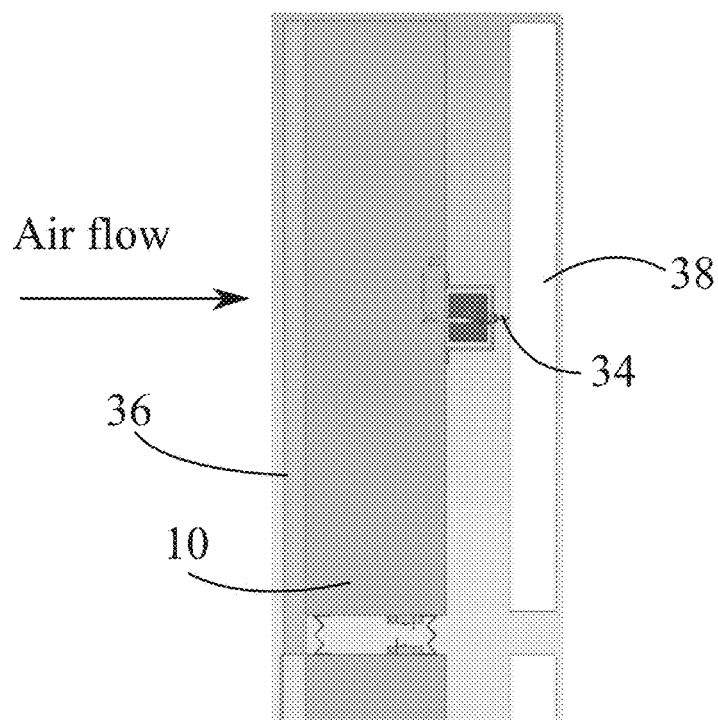
FIG. 17 shows a cross section of FIG. 16.
Figure 18:
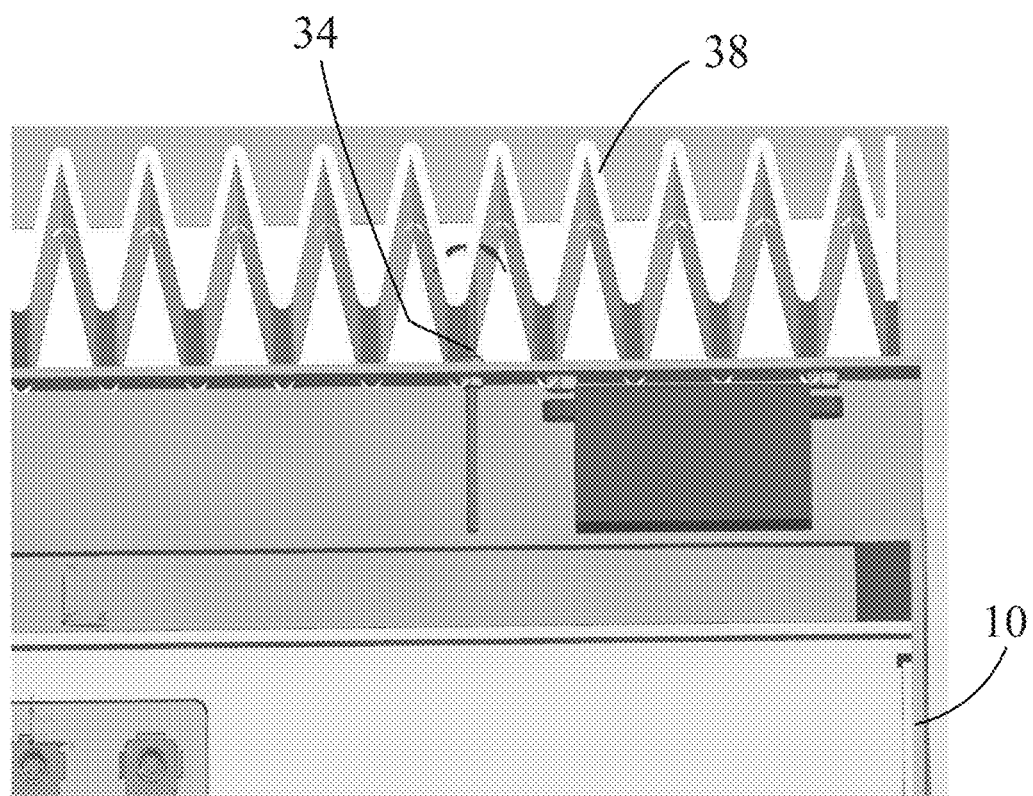
FIG. 18 shows a more detailed view of FIG. 17.

FIGS. 17 and 18 show a cross section of FIG. 16, where the air flow first meets the charging unit 10 having a protective grid 36. After the charging unit 10 in the air flow passes through a corrugated filter media 38. This media is advantageously charged with positive voltage electrodes 38 and in this case it is advantageous that the filter media 38 is at least partially conductive. The positive voltage connected to electrodes 34 varies based on material of the media but is typically in the range of 1 kV. The filter media 38 comprises advantageously two layers, namely a layer of particle filter media and of gas filter media. Further, the filter media closest to the charging unit 10 is advantageously electrically conductive either as such or combined to another layer having gas filtering properties.

Figure 19:
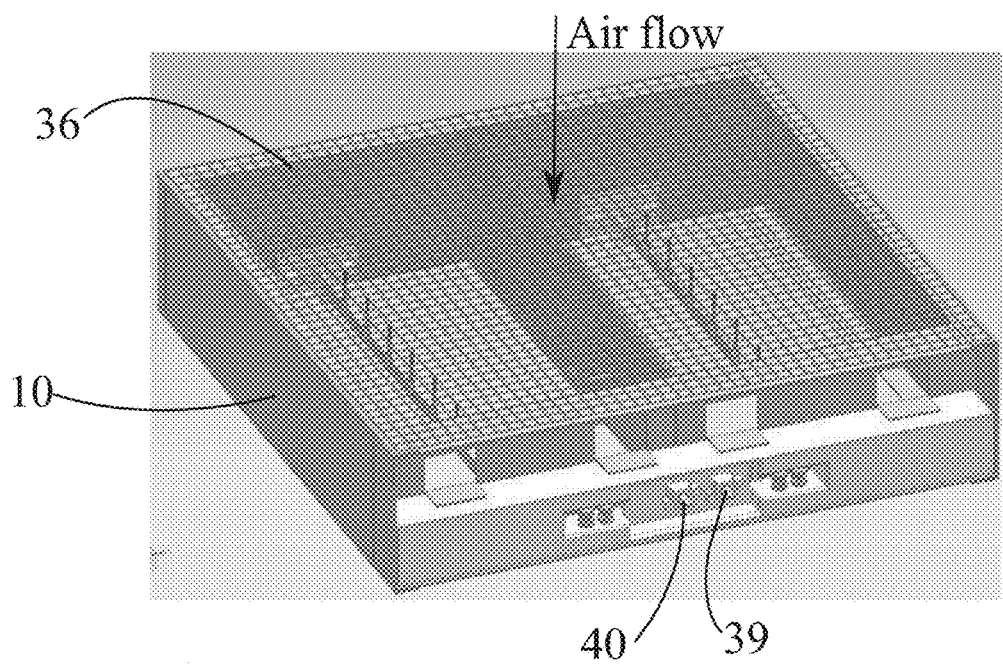
FIG. 19 shows one connectable embodiment of the charging unit to form a construction shown in FIGS. 15 and 16 in accordance with the invention.
Figure 20:
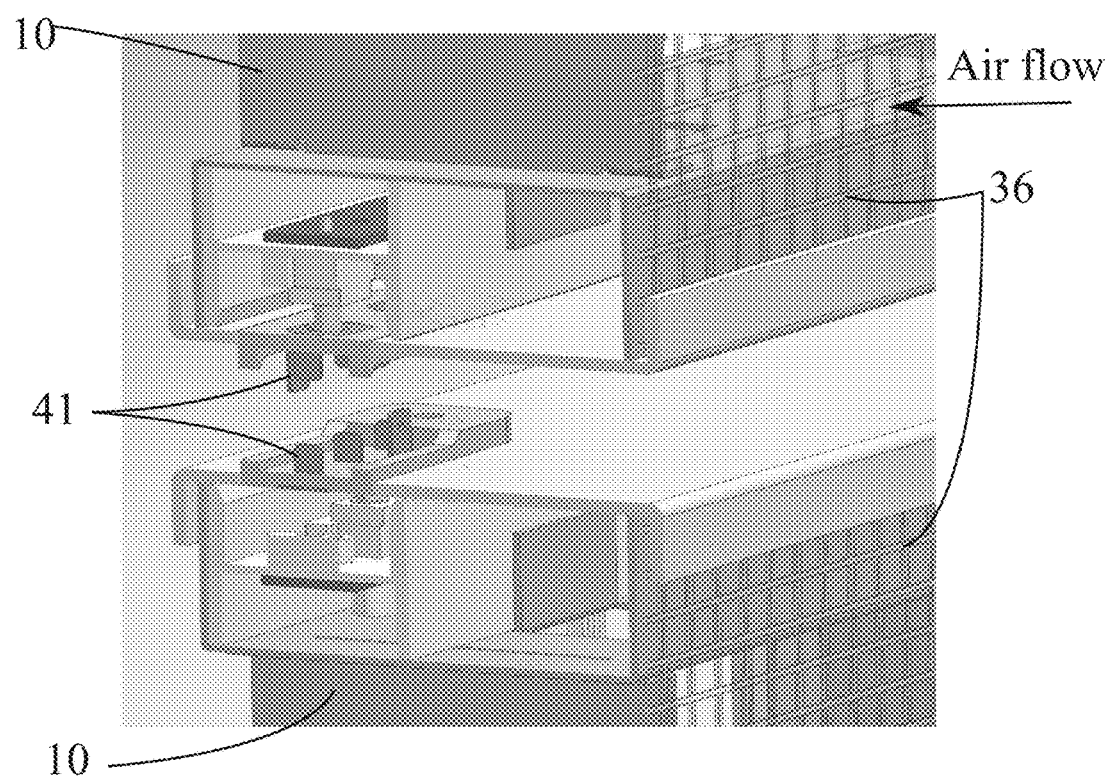
FIG. 20 shows details of the charging unit to form a construction shown in FIGS. 15 and 16 in accordance with the invention.

FIG. 19 shows one connectable embodiment of the charging unit to form a construction shown in FIGS. 15 and 16 in accordance with the invention to form a charging wall from multiple charging units 10. This is enabled by connectors for grounding 39 and negative high voltage 40 on the sides of the charging units 10 for connecting charging units next, or opposite to 10. FIG. 20 shows connectors 41 for positive voltage contacted to electrodes 34. These connectors are used as well connecting charging units next to or opposite to 25 in to each other.

Figure 21:
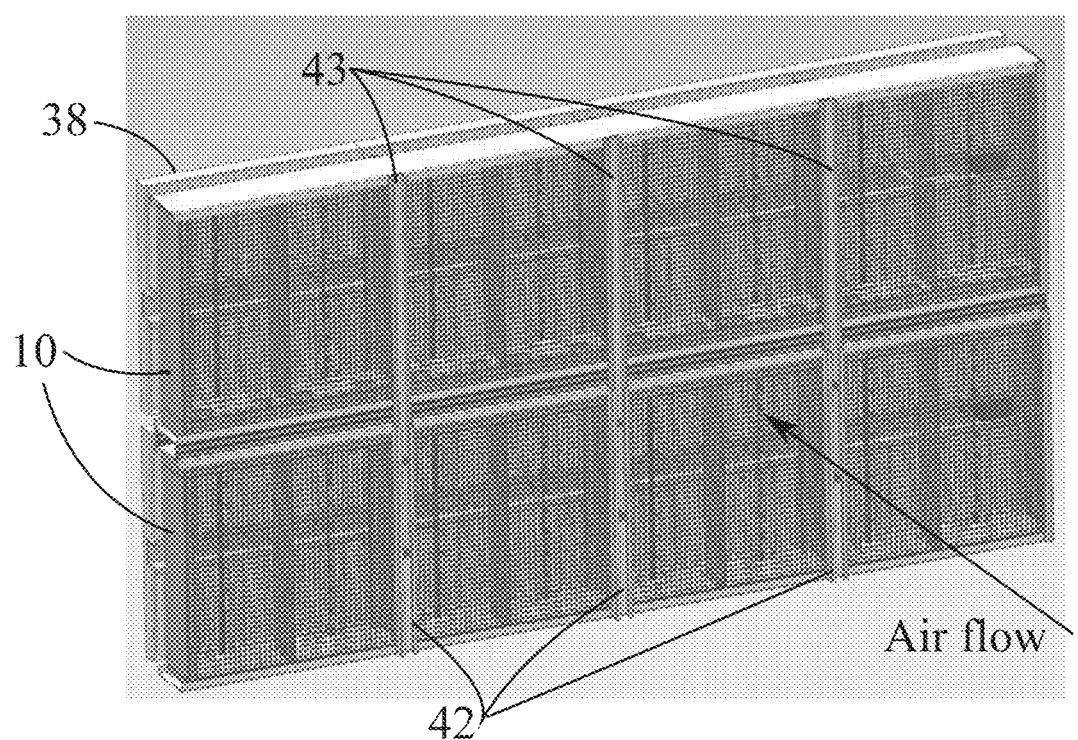
FIG. 21 shows mounting details of the charging unit to form a construction shown in FIGS. 15 and 16 in accordance with the invention.

FIG. 21 shows mounting rails 42, 43 of the invention for mounting the filtering unit to a fixed structure e.g. in front of a ventilation duct. The rails 42 are fixed to the filter structure and rails 42 slide inside the fixed rails 42 in order to make it possible to adjust the vertical position of the filter wall.

In accordance with the invention the polarities of the corona brushes 17 and positive electrodes 34 may be reversed.

In accordance with FIGS. 22 and 23 the filter unit 47 is combined with a mobile phone 45 or other mobile telecommunications device. Preferably the unit is positioned on the back side of the phone such that it does not block the camera optics 46. The inlet of the airflow 6 is on the back side of the phone 45 and the outlet preferably arranged such that it directs the air flow 6 to the face of the user. The device includes a fan 51 for producing the air flow and a high voltage unit 50 for charging the incoming air and particles preferably with help of corona brushes 17. In addition the filter comprises electrically conductive electrodes 14 covered with $TiO_2$ and preferably connected to opposite high voltage than the corona elements, preferably corona brushes 17. In addition the filter unit 47 comprises UV-light sources 16, typically LED's with corresponding transformer 49. If the voltage of the phone is suitable for the LED's the transformer may be omitted. The filter unit may also include a removable particle filter 48 and include other conductive material for filtering particle and gas contaminants. The filter unit 48 may be removable aftermarket unit or OEM part of the phone like filter phone. In addition, the unit 48 may be disposable or reusable.

Additional monitoring device 58 consists of carbon dioxide sensor 57 and/or particle sensor 56. The device is connected directly to filter units pin out 54 connector and has itself a pin 55 for further connection.

Figure 24:
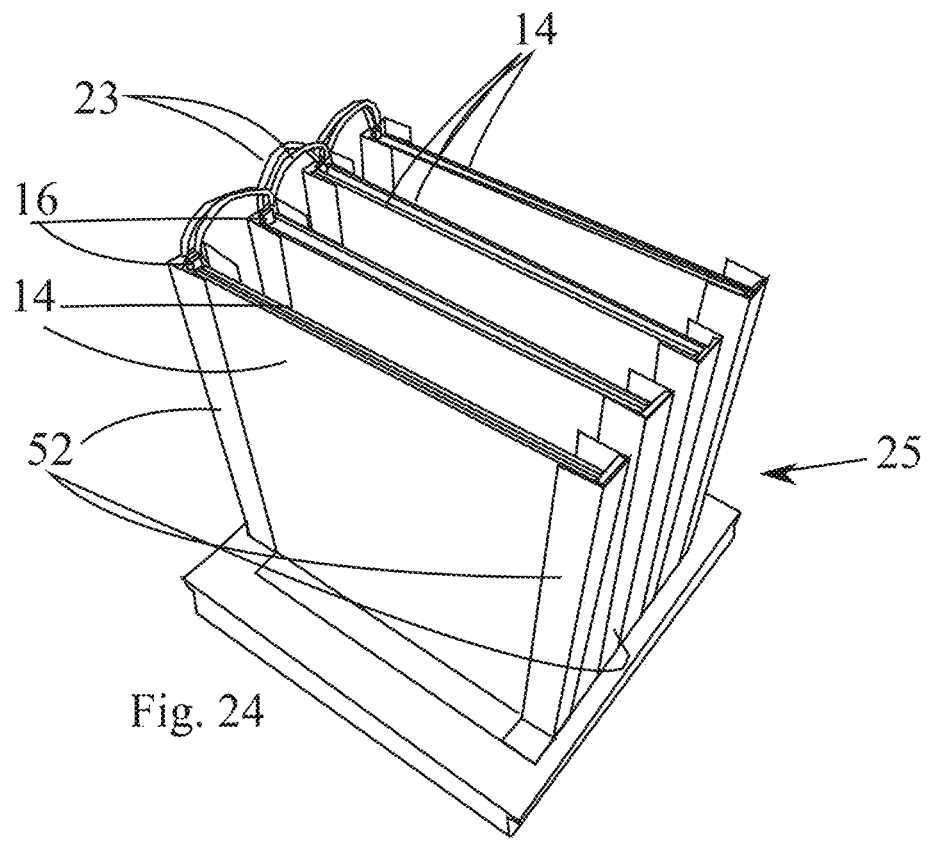
FIG. 24 shows a perspective view of an embodiment of the invention where the electrodes are formed of transparent, electrically conductive film like material.

FIG. 24 shows a perspective view of an embodiment of the invention where the electrodes 14 of the electrode unit are formed of transparent, electrically conductive film like plastic material. This plastic material is typically fixed by glue to support bars 52. Advantageously these plastic electrodes are connected to high voltage with opposite polarity than the high voltage of the charger unit. UV-leds 16 are positioned on both sides of the electrodes 14 to the support bars 52 and electrically connected with conductors 23 to supply voltage.

Figure 25:
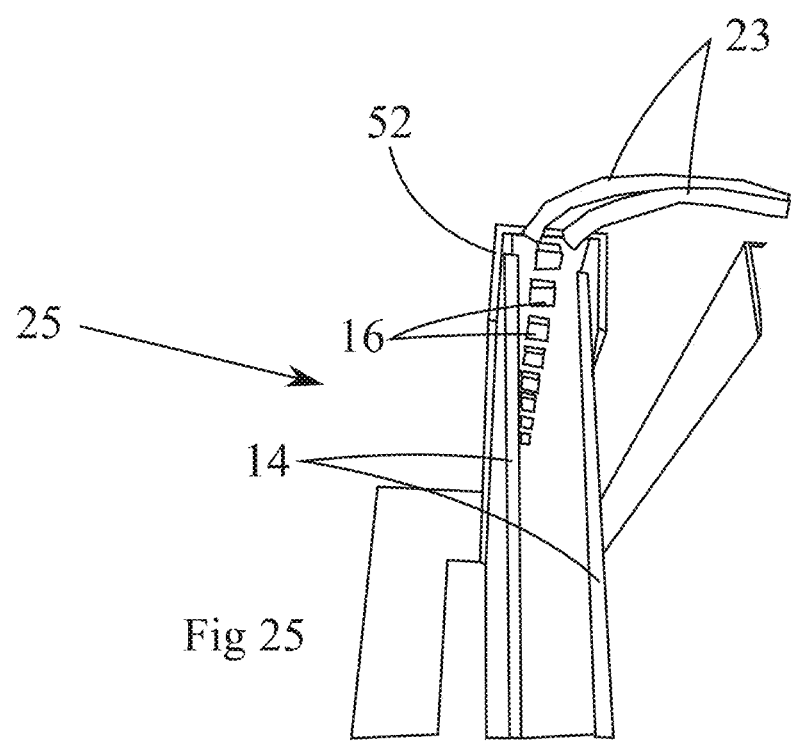
FIG. 25 shows a detail of FIG. 24.

FIG. 25 shows in more detail positioning of the LEDs inside the support bars 52, in this case support bars 52 of U-profile.

Figure 26:
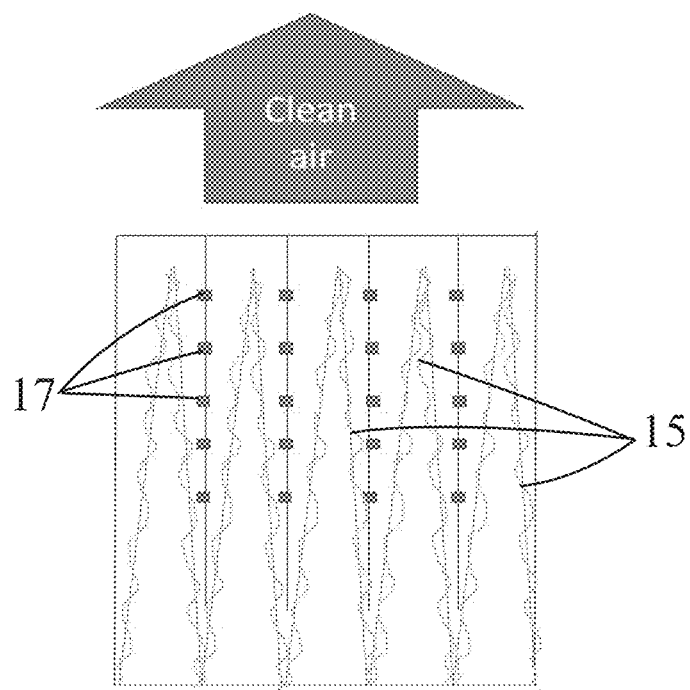
FIG. 26 shows a schematic presentation of the invention, where the $TiO_2$ coating is placed outside the filter bags with UV-light sources.
Figure 27:
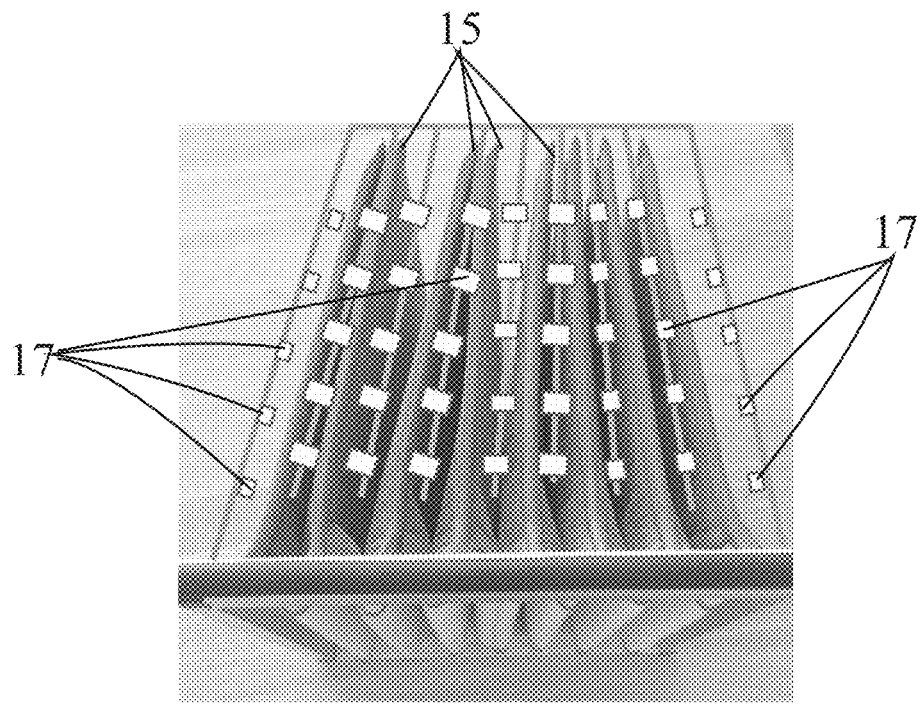
FIG. 27 shows a practical embodiment of FIG. 26.

FIG. 26 shows a schematic presentation of the invention, where the $TiO_2$ coating is placed outside the filter bags with UV-light sources 17 and FIG. 27 shows a practical embodiment of FIG. 26.

Figure 28:
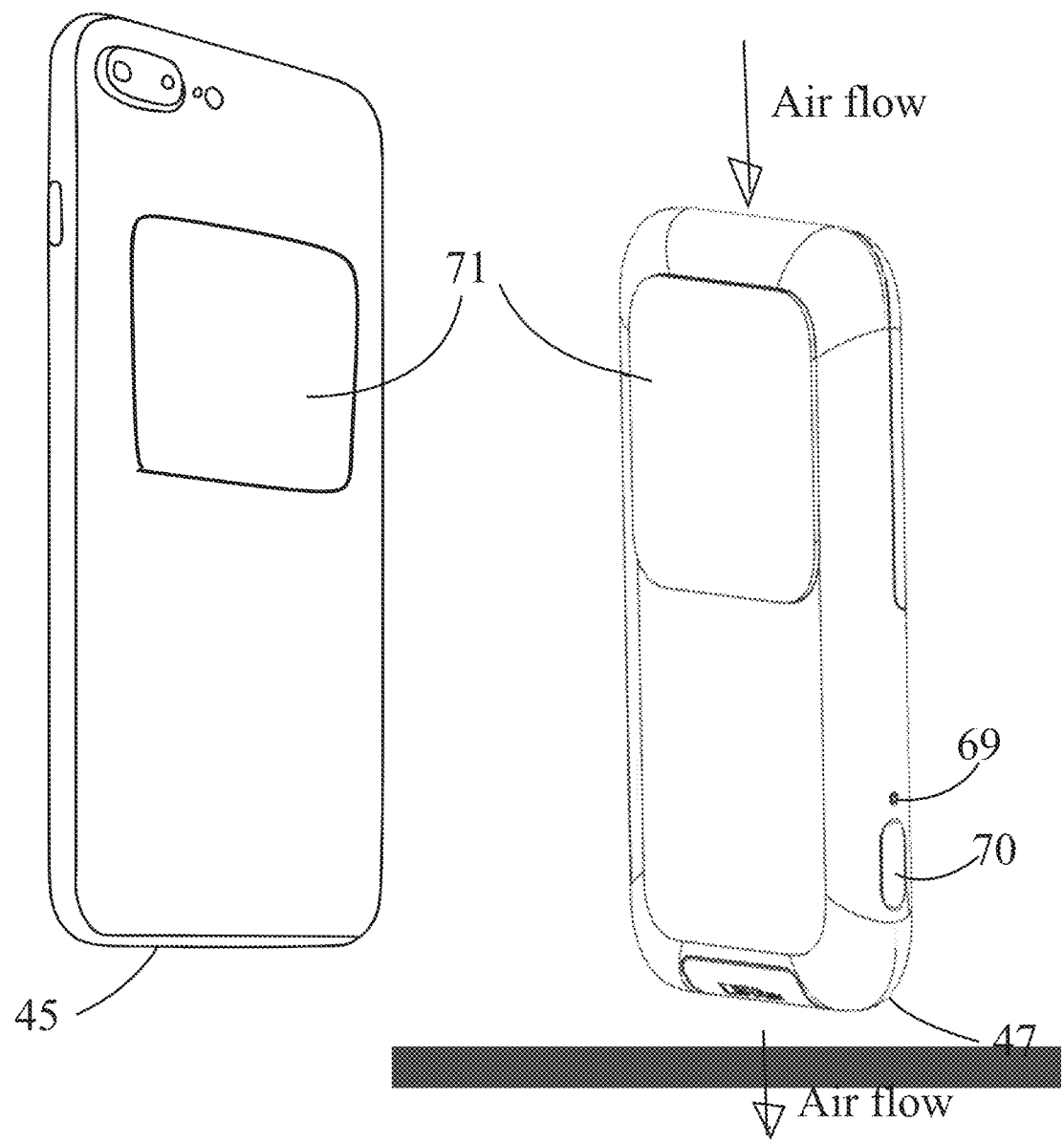
FIG. 28 shows a magnetic connection between a mobile phone and the air filter.

In FIG. 28 is shown how a mobile phone 45 may be connected to the air filter 47 in accordance with the invention. Both the mobile phone 71 and the air filter 47 include a magnetic elements 71 glued (or otherwise attached) to the mobile phone 71 and the air filter 47. The magnetic elements 71 attach to each other by a magnetic force, either in position shown in figures ore they can be attached e.g. by turning one of the elements, e.g. mobile phone 45 by 90 degrees.

Figure 29:
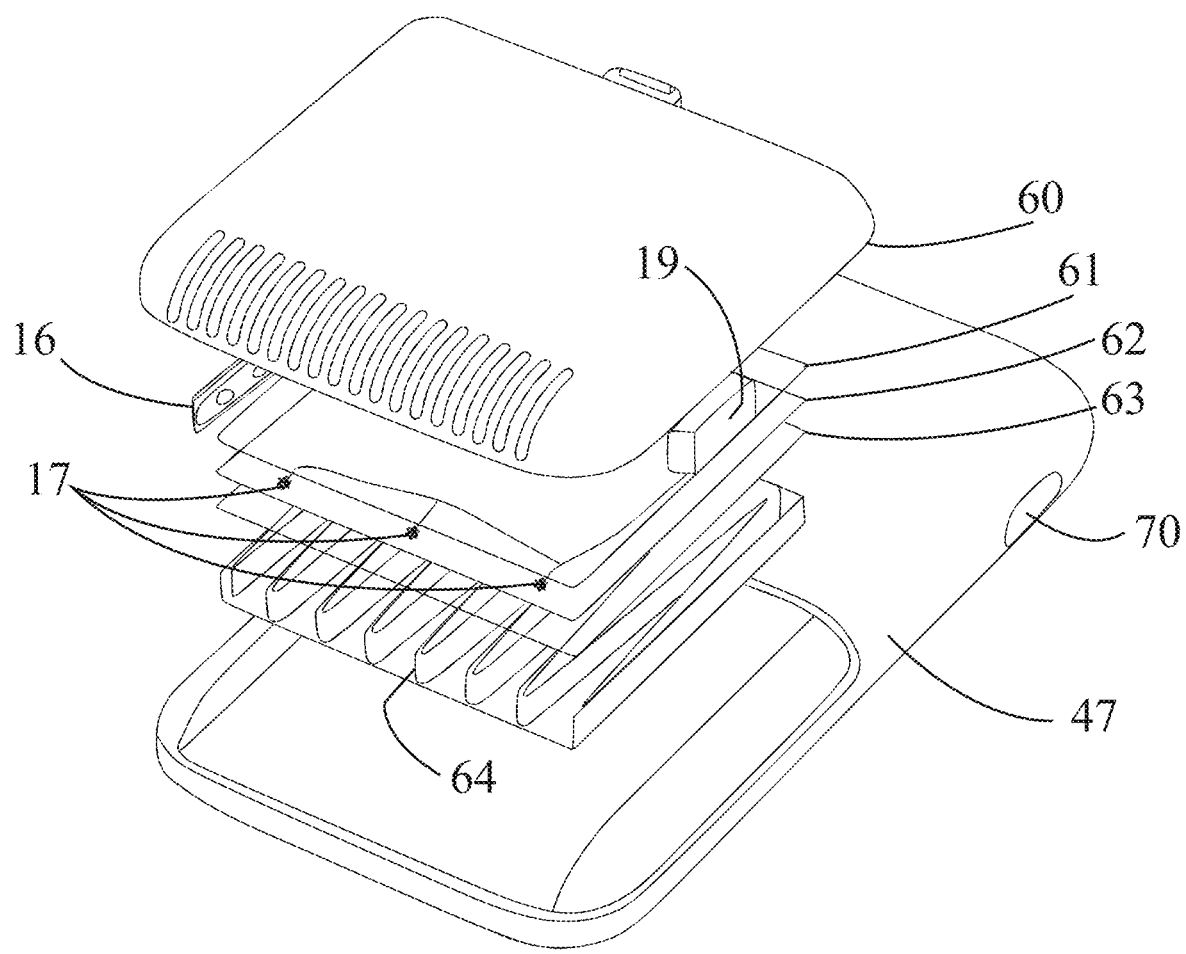
FIG. 29 shows a filter unit in accordance with the invention with a high voltage charging unit.

In FIG. 29 a filter unit 47 with a high voltage element 19 is shown in more detail. The filter unit 47 includes a filter cover 60, which may pass ultraviolet light, especially UV-A wavelengths. On a plastic sheet 60 beneath the cover 60 is positioned a plastic sheet 61 with a dot matrix printing to spread UV-light evenly to whole sheet. Below that there is a thin paper 62 and below that lid of filter material 64 and naturally below that the folded filter material 64. The main unit 47 includes the necessary electrical connections to the filter case 48.

Figure 30:
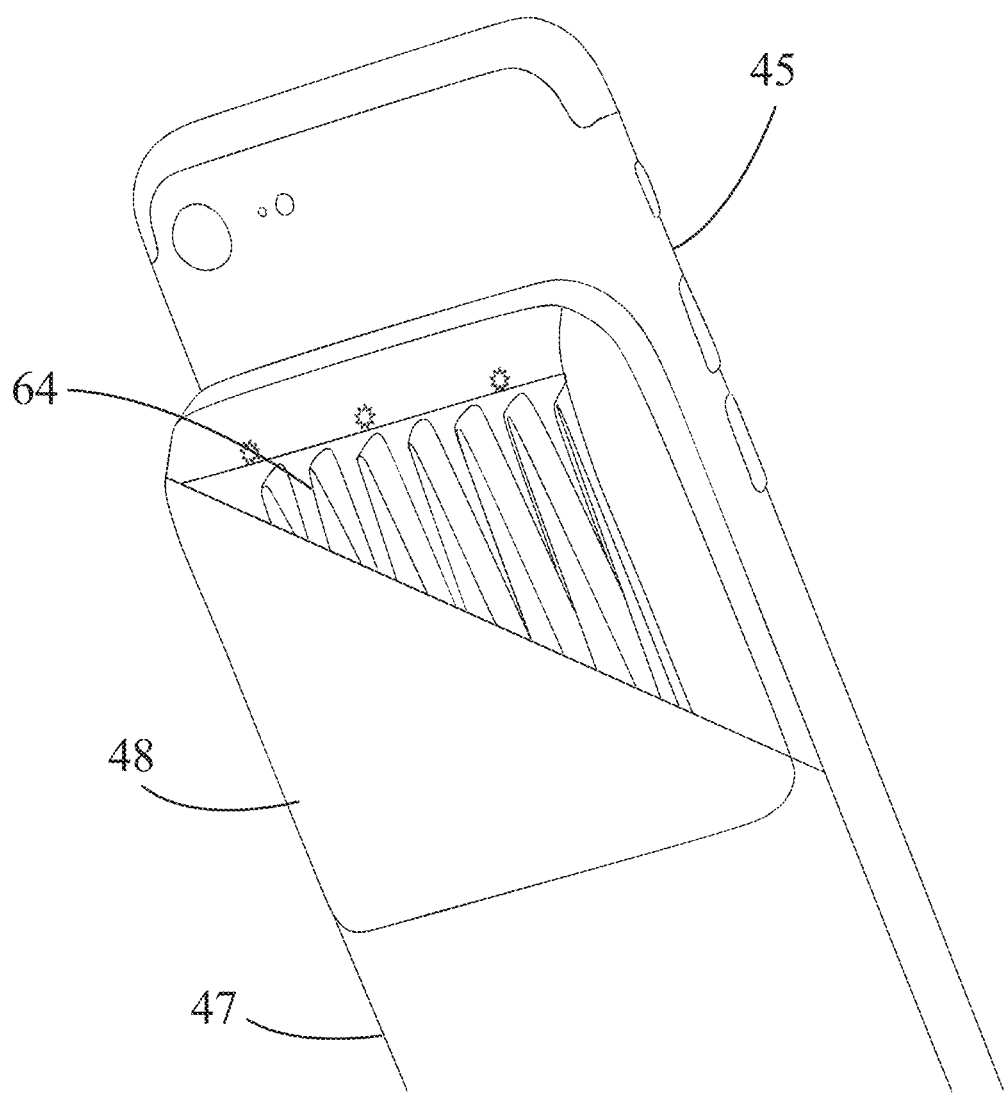
FIG. 30 shows a filter unit in accordance with the invention combined with a mobile phone.

FIG. 30 shows a filter unit 47 in accordance with the invention combined with a mobile phone 45. In the sectioned portion the filter material 64 is visible.

Figure 31:
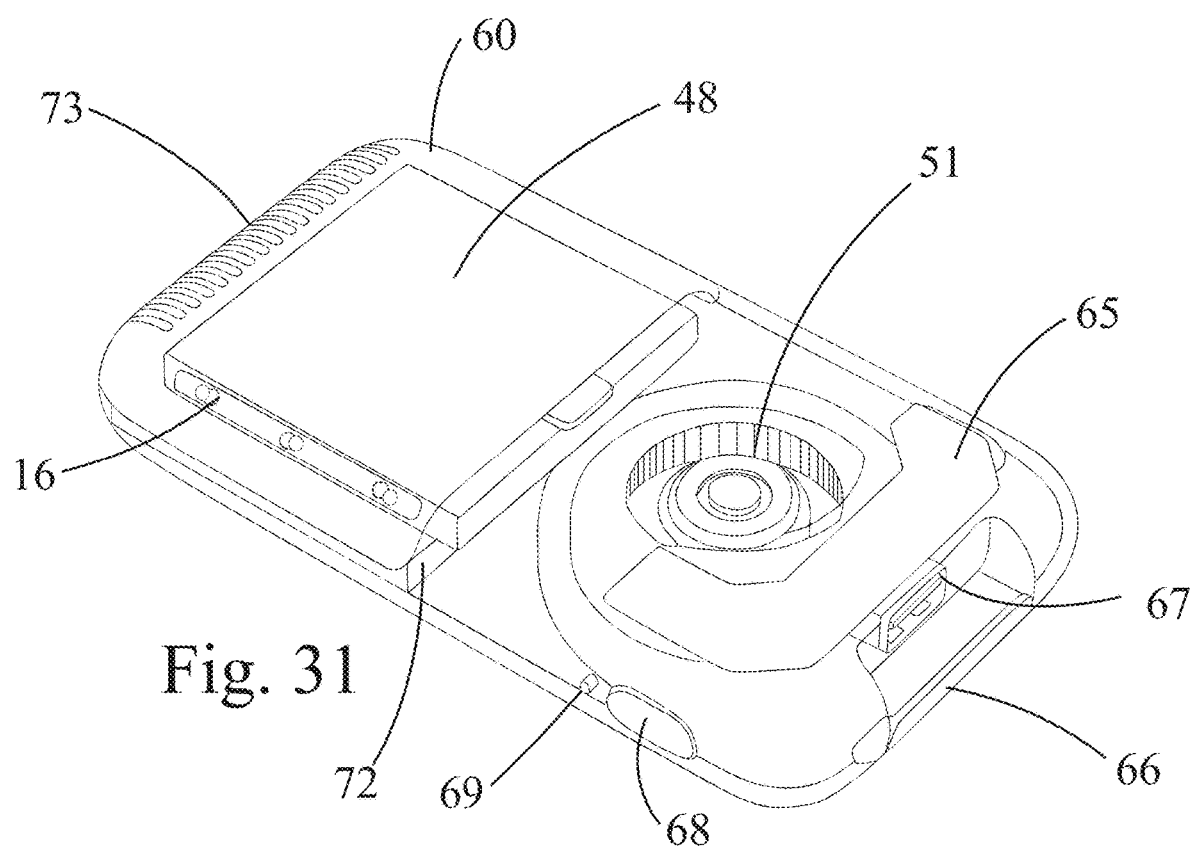
FIG. 31 shows a partially sectioned view of filter unit in accordance with the invention.

FIG. 31 shows another cross sectioned view of the air filter in accordance with the invention. Here in more detail can be seen a micro USB-port for charging the battery 72 of the filter unit. From the USB-A-port 67 the battery 72 may be used for charging other devices like the mobile phone 45 or other devices. The air filter 47 includes also a led indicator 69 for indicating the status of the air filter 47. The status may be for example on/off/charging. The air is taken in to the air filter 47 through intake grill 73 and output filtered through an exhaust hole 66. The air filter 47 includes also UV-A-LED's 16 on the side of the removable filter case 48 in order to create a photocatalytic effect with the filter material 64 including $TiO_2$ or some other photocatalytic material. UV-light may enter the filter also trough the transparent filter cover 60. The photocatalytic material may be positioned also on some layer close to the filter 64 like on layers 61, 62 or 63. The material of the filter 64 is electrically conductive in some preferred embodiments of the invention in order to make the filter material 64 an electrode.

Figure 32:
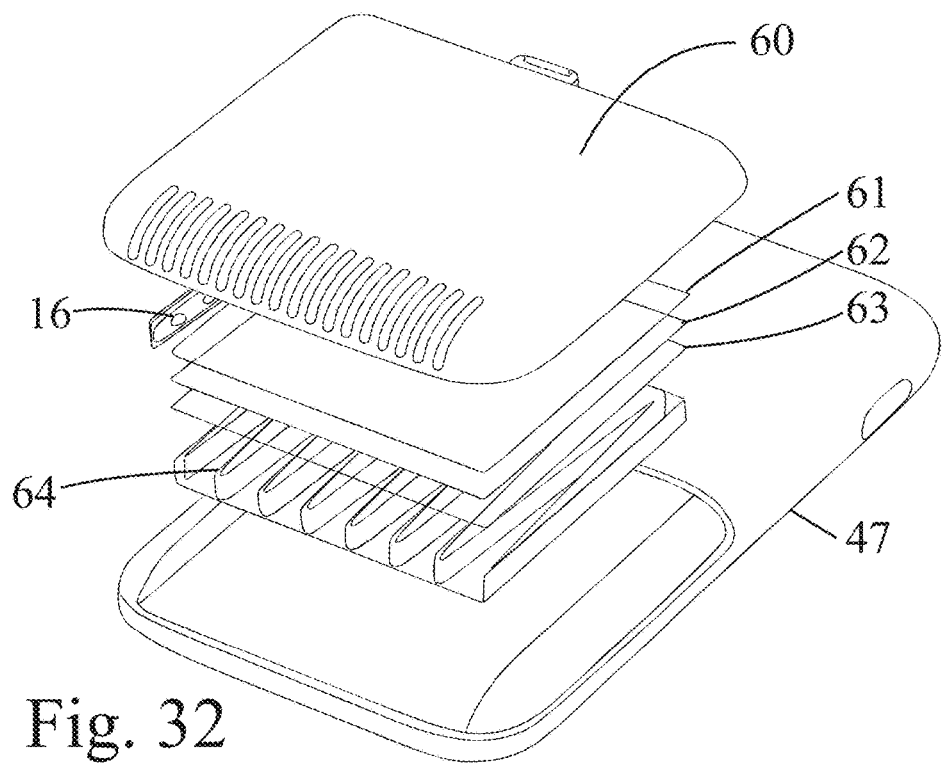
FIG. 32 shows a filter unit of FIG. 31 in more detail.

FIG. 32 shows an air filter 47 similar to air filter of FIG. 29 but without the high voltage unit 19 and corona brushes 17.

FIGS. 33 and 34 show the air flow through an air filter 47 in accordance with the invention. The unpurified air is entering the device 47 through the intake grill 73, then going through the filter unit/case 48. The air flow is created by the fan 51 (FIG. 31) by creating under pressure to the intake chamber 75 and outputting the purified air by the fan 51 to output chamber 76 and further through the exhaust hole 66 for the user. The exhaust hole may have an adjustable slider 74 for adjusting the direction and distribution of the air flow 66. The slider may also control the charging operation of the battery 72.

In FIG. 35 is presented in more detail the removable particle filter casing 48. Filter casing bottom 77 and sides 78 are from electrically conductive material. This conductive material 77, 78 is connected electrically to earth or other voltage different to the voltage of the high voltage unit 19. Preferably the polarities of the voltages of the high voltage 19 and the electrodes 77, 78 are different. Filter materials 64 are coated with $TiO_2$, Ag or similar Nano photocatalyst. Filter casing 48 is from UVA penetrable plastic sheet having uniform distribution of UV-A led light. Therefore the light 16 may illuminate both the filter casing 48 and the cover 60 of the filter unit 48 for causing the photocatalytic reaction also to the cover part 60, when it is covered with photocatalytic material like $TiO_2$. Similar sheet 63 is above filter casing 48 and between plastic sheets there is paper 62 to separate UV-LED light illumination to both sides. The paper 62 can be reflective in order to further enhance photocatalytic reaction. The paper layer 62 may have a pattern to be projected on the cover part of the filter structure 47. Casing structures 77, 78, 63, 61 and 60 can be also coated with Nano catalyst like $TiO_2$. Negative ions can be discharged from carbon fibres 79 preferably with corona brushes 17 inside or in front of filter casing in order to accelerate photocatalytic reaction. Naturally, these fibers 79 are electrically isolated from the casing structures 77, 78, 63 and 60.

In summary the top layers of the filter casing 48 are the following from top to bottom:
- 61: Cover, UV-A penetrable sheet. Can be coated with TiO2 or similar. This is the unit cover also. Even surface or with luminous distribution pattern.
- 62: Thin paper sheet for dividing LED-illumination.
- 63: Filter material cover, UV-penetrable plastic and nano-coated with TiO2 or equivalent UV-LEDs SMD type 16 assembled on printed circuit board (PCB) in the side of filter unit, illuminates both sheets 61 and 63. The LED's 16 may be on both sides of the structure 48. Carbon fibers 79 are for negative ion output.

Bottom 77 and side panels 78 are made from conductive material and either grounded or with reverse polarity than ion output 79.

Figure 36:
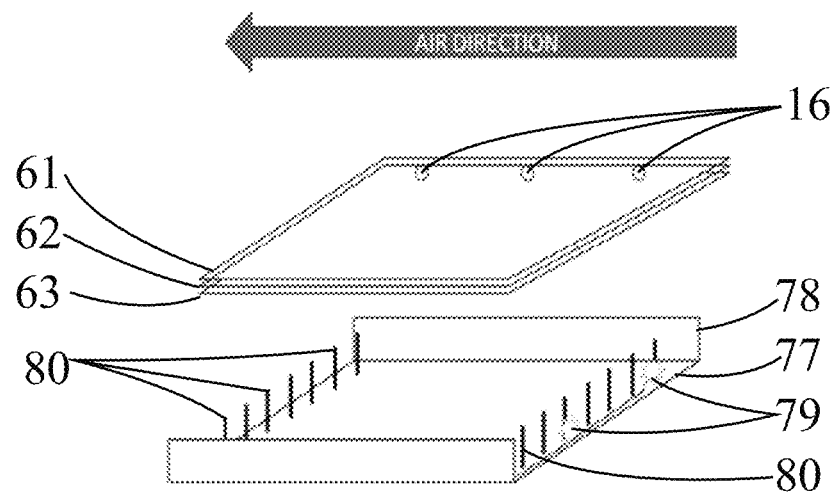

In FIG. 36 are shown guiding pins 80 for filter material 64 assembly These pns 80 allow tight connection and automated assembly process. The pins 80 are connected to their counterparts in sheet 63.

Figure 37:
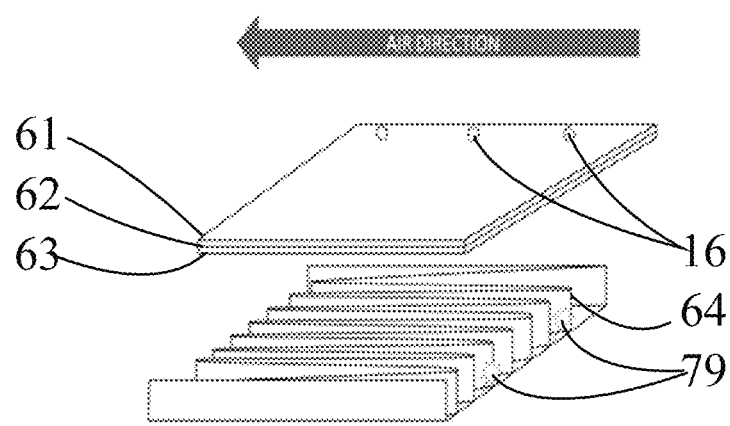

In FIG. 37 is shown in more detail how the wave like filter material is assembled in the filter casing 48. This material 64 is typically with two layers, first with particle filtering media and the second with gas adsorbent material. The filter material 64 may comprise also additional layers. The filter material 64 is coated with $TiO_2$ or equivalent material from both sides.

Figure 38:
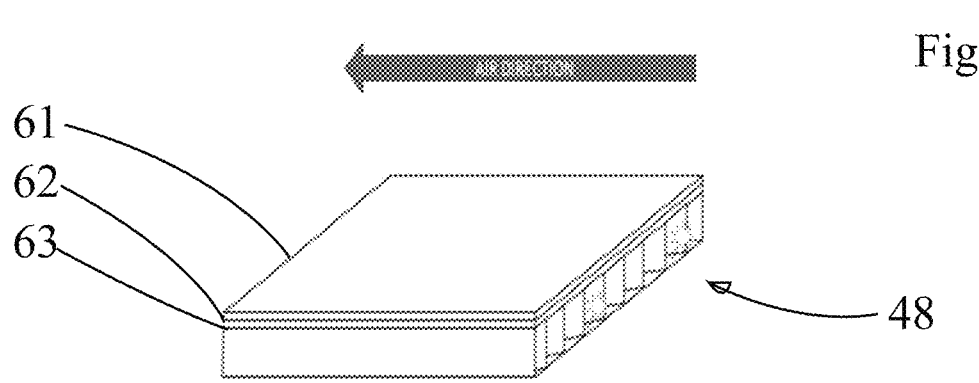

In FIG. 38 is shown the final construction.

When air purifiers (e.g. mobile communication devices in this invention) are equipped with $CO_2$ sensors, carbon dioxide levels can adjust the speed of fan 51 automatically. These units are designated to be close enough users face for enabling clean breathing zone. The $CO_2$ sensor can detect elevated $CO_2$ level and fan 51 will operate faster. When $CO_2$ level is low, air purifier goes to standby mode in order to save energy. The speed of the fan 51 may also be adjusted based on the flow resistance of the filter casing 48 such that when the flow resistance rises the speed of the fan 51 increases. The flow resistance may be determined e.g. by pressure or temperature measurement before the filter casing 48. Rising speed of motor or increased pressure or increased temperature before the filter 48 means that the filter flow resistance has increased. When the filter casing 48 is too full, e.g. the flow resistance has increased more than 30%, this situation may be indicated by a light or sound.

Instead of $TiO_2$ materials like carbon-doped titanium dioxide ($C-TiO_2$), ZnO (Jašková, Hochmannová, Vytřasová, "$TiO_2$ and ZnO Nanoparticles in Photocatalytic and Hygienic Coatings", *International Journal of Photoenergy*, vol. 2013, Article ID 795060, 6 pages, 2013.) or Nanocomposite coating of $TiO_2$ and Polytetrafluoroethylene (Kamegawa, T., Shimizu, Y. and Yamashita, H. (2012), Superhydrophobic Surfaces with Photocatalytic Self-Cleaning Properties by Nanocomposite Coating of $TiO_2$ and Polytetrafluoroethylene. Adv. Mater., 24: 3697-3700.) could be used as photo catalytic material.

The light sources 16 are advantageously LEDs typically with the following properties:
Power/led: 0.06-1 W
Wavelength in following ranges: 300-420 nm Some embodiments of the invention are defined in the following paragraphs:

Paragraph 1. An electrostatic filter construction (2) including
  a charging unit (10), which charges the particles to be filtered into a first electric potential and arranged in the filter construction (2) in the path of the air flow before filter elements (15),
  electrically conducting electrodes (14, 25) connected to a second electric potential different to the potential of the charged particles and set substantially parallel to the direction of the airflow, and
  filter elements (15) positioned after the charging unit (10) in the path of the air flow,
characterized in that
  each filter element (15) has at least one designated UV-light source (6) and an electrode (14) or grounding element (31) of photo catalytic material like $TiO_2$.

Paragraph 2. An electrostatic filter construction (2) according to Paragraph 1, characterized in that it is positioned in air ducts or ventilation channels and the filter elements (15) are bag shaped.

Paragraph 3. An electrostatic filter construction (2) according to Paragraph 1 or 2, characterized in that the bag shaped filter elements (15) are positioned around the electrodes (14), and inside the bag shaped filter elements (15) are positioned UV-light sources (16) and photo catalytic material like $TiO_2$.

Paragraph 4. An electrostatic filter construction (2) according to Paragraph for 2, characterized in that the at least one designated UV-light source (6) and an element (31) photo catalytic material like $TiO_2$ are positioned in front of the bag shaped filter element (15) in the path of the air flow (FIG. 10).

Paragraph 5. An electrostatic filter construction (2) according to Paragraphs 1-4, characterized in that the electrodes (14) are covered with photo catalytic material like $TiO_2$ or equivalent photo catalytic material and connected electrically to ground potential or to opposite polarity than high voltage unit for corona discharge before it.

Paragraph 6. An electrostatic filter construction (2) according to any previous Paragraph, characterized in that the charging unit (10) comprises corona strips (20) including brush like extensions (17) directed against the air flow.

Paragraph 7. An electrostatic filter construction (2) according to any of the above Paragraphs, characterized in that the corona strips (20) are connected to negative high voltage.

Paragraph 8. An electrostatic filter construction (2) according to any of the above Paragraphs, characterized in that the bag shaped filter (15) comprises a layer of particle filter media (27) and of gas filter media (28).

Paragraph 9. An electrostatic filter construction (2) according to any of the above Paragraphs, characterized in that the bag shaped filter (15) comprises multiple subfilters (30).

Paragraph 10. An electrostatic filter construction (2) according to any of the above Paragraphs, characterized in that the bag shaped filters (15) are disposable.

Paragraph 11. An electrostatic filter construction (2) according to any of the above Paragraphs, characterized in that inside the bag shaped filters (15) are electrodes (34) connected to a voltage, the polarity of which is opposite to the voltage of the charging unit (10).

Paragraph 12. An electrostatic filter construction (2) according to any of the above Paragraphs, characterized in that the bag shaped filters (27) are made of electrically conducting material.

Paragraph 13. An electrostatic filter construction (2) according to any of the above Paragraphs, characterized in that one side of the bag shaped filters (27) is covered with $TiO_2$ and this side is exposed to UV-light.

Paragraph 14. An electrostatic filter construction (2) according to any of the above Paragraphs, characterized in that the filter construction (2) is connected to a mobile communication device.

Paragraph 15. An electrostatic filter construction (2) according to Paragraph 13, characterized in that the filter construction is an integral part of the mobile communication device.

Paragraph 16. An air cleaning method, where an air flow is created and which method comprises steps for
 charging the particles to be filtered into a first electric potential before they enter filter elements (15),
 attracting the charged particles by electrically conducting electrodes (14, 31) connected to a second electric potential different to the potential of the charged particles and set substantially parallel to the direction of the airflow, and
 guiding the charged air through filter elements (15) positioned after the charging unit (10) in the path of the air flow.
characterized in that
 directing UV-light in or close to each bag shaped filter element (15) and placing the photo catalytic material like $TiO_2$ close to the UV-light.

Paragraph 17. An air cleaning method according to Paragraph 16, characterized in that it is used for ducts or ventilation channels and the filter elements (15) are bag shaped.

Paragraph 18. An air cleaning method according to Paragraph 16 or 17, characterized in positioning the bag shaped filter elements (15) around the electrodes (14), and positioning inside the bag shaped filter elements (15) UV-light sources (16) and photo catalytic material like $TiO_2$.

Paragraph 19. An air cleaning method according to Paragraph 16 or 17, characterized in positioning the at least one designated UV-light source (6) and an element (31) photo catalytic material like $TiO_2$ in front of the bag shaped filter element (15) in the path of the air flow (FIG. 10).

Paragraph 20. An air cleaning method according to Paragraph 16-19, characterized in covering the electrodes (14) with photo catalytic material like $TiO_2$ or equivalent photo catalytic material and connecting them electrically to ground potential.

Paragraph 21. An air cleaning method according to any previous method Paragraph, characterized in that the charging unit (10) comprises corona strips (20) including brush like extensions (17) directed against the air flow.

Paragraph 22. An air cleaning method according to any previous method Paragraph, characterized in that the corona strips (20) are connected to negative high voltage.

Paragraph 23. An air cleaning method according to any previous method Paragraph, characterized in that the bag shaped filter (15) comprises a layer of particle filter media (27) and of gas filter media (28).

Paragraph 24. An air cleaning method according to any previous method Paragraph, characterized in that the bag shaped filter (15) comprises multiple subfilters (30).

Paragraph 25. An air cleaning method according to any previous method Paragraph, characterized in that the bag shaped filters (15) are disposable.

Paragraph 26. An air cleaning method according to any of the above method Paragraphs, characterized in that inside the bag shaped filters (15) are electrodes (34) connected to a voltage opposite to the voltage of the charging unit (10, 25).

Paragraph 27. An air cleaning method according to any of the above method Paragraphs, characterized in that the bag shaped filters (27) are made of electrically conducting material.

Paragraph 28. An air cleaning method according to any of the above method Paragraphs characterized in that one side of the bag shaped filters (27) is covered with $TiO_2$ and this side is exposed to UV-light.

Paragraph 29. An air cleaning method according to any of the above Paragraphs, characterized in that the filter construction (2) is connected to a mobile communication device.

Paragraph 30 An air cleaning method according to Paragraph 27, characterized in that the filter construction (2) is an integral part of the mobile communication device.

Paragraph 31. A mobile filter unit including
 a mobile communication device (45),
characterized in that it further includes
 a filter unit (47) connected to the mobile communication device (45) including
  a fan (51) for generating an air flow (6) from behind of the mobile communication device (45),
  high voltage unit (50, 17) for charging the air flow (6) and its particles,
  $TiO_2$-covered electrodes (16) in the air flow (6) connected to opposite polarity than the high voltage unit (50, 17),
  UV-LEDs (16) illuminating the electrodes (16), and
  outlet (53) for the air flow directed in direction of user of the mobile communication device (45).

Paragraph 32. A mobile filter unit in accordance with paragraph 31, characterized in that the electrodes (16) are as filter consumable filter unit and the electrodes are from aluminium, plastic or other suitable conductive materials and are forming a low pressure drop form like honeycomb, mesh, fins, pleated etc.

Paragraph 33. A mobile filter unit in accordance with paragraph 31 or 32, characterized in that it includes a removable particle filter.

The invention claimed is:
1. A mobile filter unit comprising:
a mobile communication device, and
a filter unit connected to the mobile communication device,
wherein the filter unit comprises:
a fan for generating an air flow from behind of the mobile communication device,
a filter material, wherein said filter material is folded, electrically conductive, and covered with $TiO_2$, wherein said filter material is configured to act as an electrode,
a high voltage unit for charging the air flow and particles within the air flow,
UV-LEDs illuminating the electrode,
an air inlet, and an outlet for the air flow directed in direction of user of the mobile communication device, the electrode being in the air flow and connected to an opposite polarity than the high voltage unit.

2. The mobile filter unit in accordance with claim 1, wherein the electrode is a consumable filter unit comprising aluminium, plastic or other suitable conductive materials and wherein the electrode is configured to provide a low pressure drop.

3. The mobile filter unit in accordance with claim 1, further comprising a removable particle filter.

4. The mobile filter unit in accordance with claim 1, further comprising a magnetic connection between the filter unit and the mobile communication device.

5. The mobile filter unit in accordance with claim 1, further comprising a battery having connections both for charging from and loading to other devices.

6. The mobile filter unit in accordance with claim 1, further comprising a changeable filtration unit.

7. The mobile filter unit in accordance with claim 1, further comprising a slider for adjusting the direction of the output air flow.

8. A mobile filter unit connectable to a mobile communication device, the mobile filter unit comprising:
- a fan for generating an air flow inside the filter unit,
- a filter material which is folded, electrically conductive, and covered with a photo catalytic material and wherein said filter material is configured to act as an electrode,
- a high voltage unit for charging the air flow and particles within the air flow,
- UV-LEDs illuminating the electrodes,
- an air inlet,
- a magnetic connection between the filter unit and the mobile communication device, and
- an outlet for the air flow directed in the direction of a user of the filter unit,
- the electrode being in the air flow and connected to an opposite polarity than the high voltage unit.

9. The mobile filter unit in accordance with claim 8, wherein the electrode is a consumable filter unit comprising aluminium, plastic or other suitable conductive materials and wherein the electrode is configured to provide a low pressure drop.

10. The mobile filter unit in accordance with claim 8, further comprising a removable particle filter.

11. The mobile filter unit in accordance with claim 8, further comprising a battery having connections both for charging from and to other devices.

12. The mobile filter unit in accordance with claim 8, further comprising a changeable filtration unit.

13. The mobile filter unit in accordance with claim 8, further comprising a slider for adjusting the direction and distribution of the output air flow.

14. The mobile filter unit in accordance with claim 8, further comprising magnets for attaching the filter unit to a communications device.

15. The mobile filter unit in accordance with claim 8, wherein the filter is wave formed and electrodes which are positioned substantially parallel to the direction of flow of the gas are equipped with ultraviolet light sources and covered with photo catalytic material.

16. The mobile filter unit in accordance with claim 8, wherein brush-like corona elements are used for charging incoming particles.

17. The mobile filter unit in accordance with claim 8, further comprising means for forcing the incoming air to contact $TiO_2$ or other catalyst grounded or covered electrodes by using opposite polarity than the high voltage used for charging the incoming air flow.

18. The mobile filter unit in accordance with claim 8, wherein the filter material bottom and sides are electrically conductive material.

19. The mobile filter unit in accordance with claim 8, further comprising a filter casing from UVA penetrable plastic sheet having essentially uniform distribution for UVA led light.

20. The mobile filter unit in accordance with claim 19, wherein the structures forming the filter casing are coated with $TiO_2$, Ag or similar Nano catalyst material.

21. The mobile filter unit in accordance with claim 8, wherein the mobile filter unit is equipped with a $CO_2$ sensor and means for adjusting the speed of the fan based on the $CO_2$ content such that the higher $CO_2$ content corresponds to a higher fan speed.

22. The mobile filter unit in accordance with claim 8, wherein a filter casing is connected to a second electric potential different to the potential of the charged particles and set substantially parallel to the direction of the airflow.

23. A filter casing for a mobile filter unit comprising:
- a housing with openings for air flow, and
- filter material inside the housing,
- a high voltage unit for charging the air flow and particles wherein
the housing is:
- at least partially transparent to UV-light,
- electrically conductive, and
- covered at least partially with photocatalytic material, and the filter material is:
- folded, electrically conductive, and covered at least partially with photocatalytic material, and wherein said filter material is configured to act as an electrode, the electrode being in the air flow and connected to opposite polarity than the high voltage unit, wherein the filter casing further comprises UV-LEDS illuminating the electrode.

24. The filter casing in accordance with claim 23, wherein above the housing is positioned a paper sheet for dividing illumination and above said sheet is positioned a UV-penetrable sheet acting as a case cover.

25. The filter casing in accordance with claim 23, wherein the filter material is two layered, one for particles and the other for gaseous material.

26. The filter casing in accordance with claim 23, wherein the housing is electrically connected to a desired potential when the casing is connected to a filter unit either by surface contact or by a connector.

27. The mobile filter unit in accordance with claim 2, wherein the electrode is configured to provide a low pressure drop by comprising a honeycomb, mesh, fins, or pleated form.

28. The mobile filter unit in accordance with claim 9, wherein the electrode is configured to provide a low pressure drop by comprising a honeycomb, mesh, fins, or pleated form.

* * * * *